(12) United States Patent
Ferguson et al.

(10) Patent No.: US 12,016,682 B2
(45) Date of Patent: Jun. 25, 2024

(54) IN-VIVO MONITORING OF MOLECULAR TARGETS

(71) Applicant: The Regents of the University Of California, Oakland, CA (US)

(72) Inventors: Brian Scott Ferguson, Goleta, CA (US); Hyongsok Tom Soh, Santa Barbara, CA (US); David A. Hoggarth, Toronto (CA)

(73) Assignee: The Regents of the University of California, Oakland, CA (US)

( * ) Notice: Subject to any disclaimer, the term of this patent is extended or adjusted under 35 U.S.C. 154(b) by 779 days.

(21) Appl. No.: 14/768,134

(22) PCT Filed: Jan. 29, 2014

(86) PCT No.: PCT/US2014/013620
§ 371 (c)(1),
(2) Date: Aug. 14, 2015

(87) PCT Pub. No.: WO2014/143427
PCT Pub. Date: Sep. 18, 2014

(65) Prior Publication Data
US 2016/0166186 A1 Jun. 16, 2016

Related U.S. Application Data

(60) Provisional application No. 61/784,130, filed on Mar. 14, 2013.

(51) Int. Cl.
*A61B 5/145* (2006.01)
*A61B 5/00* (2006.01)
(Continued)

(52) U.S. Cl.
CPC ...... *A61B 5/14525* (2013.01); *A61B 5/14546* (2013.01); *A61B 5/1473* (2013.01);
(Continued)

(58) Field of Classification Search
CPC ............ A61B 5/14532; A61B 5/14546; A61B 5/14735; A61B 5/4839; C12Q 2525/205; C12Q 2565/629
See application file for complete search history.

(56) References Cited

U.S. PATENT DOCUMENTS

2006/0014172 A1* 1/2006 Muller ................... B82Y 5/00
435/6.11
2007/0031283 A1* 2/2007 Davis ............... A61B 5/150221
422/400
(Continued)

FOREIGN PATENT DOCUMENTS

WO WO 2011056185 5/2011

OTHER PUBLICATIONS

McGrath et al., The use of differential measurements with a glucose biosensor for interference compensation during glucose determinations by flow injection analysis. Biosensors and Bioelectronics. vol. 10, Issues 9-10, pp. 937-943 (Year: 1995).*
(Continued)

*Primary Examiner* — Tse W Chen
*Assistant Examiner* — Michael A Catina
(74) *Attorney, Agent, or Firm* — Edward J. Baba; Michael J. Blessent; Bozicevic, Field & Francis LLP

(57) ABSTRACT

The present disclosure provides devices, methods and systems for analyte detection and/or monitoring, e.g., the continuous and/or semi-continuous monitoring of in-vivo analyte concentrations in real time. Generally, the devices, methods and systems of the present disclosure make use of signaling probes; methods or devices for reducing interferent-based fouling of the signaling probes, non-specific binding to the signaling probes and/or occlusion of a sensor surface; and methods and/or devices for providing an adjusted signal based on a detected signal from the signaling
(Continued)

probes. Compositions including conformation switching signaling probes are also provided.

22 Claims, 18 Drawing Sheets

Specification includes a Sequence Listing.

(51) Int. Cl.
    *A61B 5/1473*     (2006.01)
    *A61B 5/15*     (2006.01)
    *C12N 15/11*     (2006.01)
    *C12N 15/115*     (2010.01)
    *C12Q 1/6816*     (2018.01)

(52) U.S. Cl.
    CPC .... *A61B 5/14735* (2013.01); *A61B 5/150992* (2013.01); *A61B 5/4839* (2013.01); *C12N 15/111* (2013.01); *C12N 15/115* (2013.01); *C12Q 1/6816* (2013.01); *A61B 2503/40* (2013.01); *A61B 2503/42* (2013.01); *C12N 2310/16* (2013.01); *C12N 2320/10* (2013.01)

(56) References Cited

U.S. PATENT DOCUMENTS

| | | |
|---|---|---|
| 2009/0170718 A1 | 7/2009 | Soh et al. |
| 2011/0003303 A1 | 1/2011 | Pagano et al. |
| 2012/0116195 A1 | 2/2012 | Chaum et al. |

OTHER PUBLICATIONS

Cass et al. "Nucleic acid aptamers: ideal reagents for point-of-care diagnostics" Faraday Discuss., 2011, 149, 49-61 (Year: 2011).*
Zuo et al. "A Target-Responsive Electrochemical Aptamer Switch (TREAS) for Reagentless Detection of Nanomolar ATP" J. Am. Chem. Soc. 2007, 129, 5, 1042-1043 (Year: 2007).*
Ahuja, A. S., et al; (1978) "Transport phenomena in laminar flow of blood"; *Physics in medicine and biology 23*, 928-936.
Al-Nazawi, M. H. & Homeida, A. M.; (2008) "Comparative Pharmacokinetic Studies of Kanamycin in Camels, Sheep and Goats"; *Scientific Journal of King Faisal University(Basic and Applied Sciences)* 10, pp. 105-113.
Andrade, J. D. & Hlady, V.; (1986) "Protein adsorption and materials biocompatibility: a tutorial review and suggested hypotheses"; *Advances in Polymer Science 79*; pp. 1-63.
Anker, J. N. et al. (2008) "Biosensing with plasmonic nanosensors"; *Nature materials 7*, pp. 442-453.
Baker, D. A. & Gough, D. A. (1995) "A Continuous, Implantable Lactate Sensor"; *Analytical Chemistry 67*; pp. 1536-1540.
Baldrich, E., et al; (2004) "Aptasensor development: elucidation of critical parameters for optimal aptamer performance"; *Analytical chemistry 76*; pp. 7053-7063.
Bird et al., (1988) "Single-chain antigen-binding proteins"; *Science*, 242; pp. 423-426.
Brody, James P and Yager Paul; (1997) "Diffusion Based Extraction in A Microfabricated Device"; *Sensors and Actuators A: Physical 58*; pp. 13-18.
Camaggi, C., et al; (1988) "Epirubicin and doxorubicin comparative metabolism and pharmacokinetics"; *Cancer chemotherapy 21*; pp. 221-228.
Chen, S.J. et al. (2008) "Colorimetric determination of urinary adenosine using aptamer-modified gold nanoparticles"; *Biosensors& bioelectronics 23*; pp. 1749-1753.
Colcher David, et al; (1990) "In vivo tumor targeting of a recombinant single-chain antigen-binding protein"; *J Natl Cancer Inst.* 82(14); pp. 1191-1197.

Das Thakur, M. et al; (2013) "Modelling vemurafenib resistance in melanoma reveals a strategy to forestall drug resistance"; *Nature* 494(7436); pp. 251-255.
Desoize, B. & Robert, J.; (1994) "Individual dose adaptation of anticancer drugs"; .*European journal of cancer 30A*; pp. 844-851.
Dobbs, N. et al; (1995) "Gender affects doxorubicin pharmacokinetics in patients with normal liver biochemistry"; *Cancer chemotherapy and pharmacology 36*; pp. 473-476.
Edmonson, J. H. et al; (1993) "Randomized comparison of doxorubicin alone versus ifosfamide plus doxorubicin or mitomycin, doxorubicin, and cisplatin against advanced soft tissue sarcomas. Journal of clinical oncology": *Official Journal of the American Society of Clinical Oncology 11*; pp. 1269-1275.
Eikenberry, S. (2009) "A tumor cord model for doxorubicin delivery and dose optimization in solid tumors"; *Theoretical Biology and Medical Modelling 2009*, 6:16; pp. 1-20.
Elias, A. et al; (1989) "Response to mesna, doxorubicin, ifosfamide, and dacarbazine in 108 patients with metastatic or unresectable sarcoma and no prior chemotherapy"; *Journal of clinical oncology: official journal of the American Society of Clinical Oncology 7*; pp. 1208-1216.
Elis, A. et al; (2010) "Doxorubicin in lymphoma: association between pharmacokinetic variability and clinical response"; *Therapeutic drug monitoring 32*; pp. 50-52.
Fan, C., et al; (2003) "Electrochemical interrogation of conformational changes as a reagentless method for the sequence-specific detection of DNA"; *Proceedings of the National Academy of Sciences of the United States of America 100*; pp. 9134-9137.
Ferguson Brian Scott; "Development of Novel Integrated Microfluidic Electrochemical Point-of-Care Sensors for Pathogen Detection and Continuous Drug Monitoring"; *Dissertation Abstracts International*, vol. 72, Issue 08; (Mar. 2011); pp. 1-114.
Frost, M. C. et al; (2002) "Implantable chemical sensors for real-time clinical monitoring: progress and challenges"; *Current opinion in chemical biology 6*; pp. 633-641.
Gaster, R. S. et al; (2009) "Matrix-insensitive protein assays push the limits of biosensors in medicine"; *Nature medicine 15*; pp. 1327-1332.
Grabowski, E. F., et al; (1972) "Effects of shear rate on the diffusion and adhesion of blood platelets to a foreign surface"; *Industrial& Engineering Chemistry Fundamentals 11*; pp. 224-232.
Greene, R. F., et al; (1983) "Plasma pharmacokinetics of adriamycin and adriamycinol: implications for the design of in vitro experiments and treatment protocols"; *Cancer research 43*; pp. 3417-3421.
Hamburg, M. A. et al; (2010) "The path to personalized medicine"; *The New England journal of medicine 363*; pp. 301-304.
Hunkapiller and Hood, (1986) "Immunology: The growing immunoglobulin gene superfamily" *Nature*, 323; pp. 15-16.
Huston et al.; (1988) "Protein engineering of antibody binding sites: recovery of specific activity in an anti-digoxin single-chain Fv analogue produced in *Escherichia coli*" *Proc. Natl. Acad. Sci. USA.*, 85; pp. 5879-5883.
Kang, D. et al; (2009) "Comparing the properties of electrochemical-based DNA sensors employing different redox tags"; *Analytical chemistry 81*; pp. 9109-9113.
Keller, T. et al. (2009) "Sensitive troponin I assay in early diagnosis of acute myocardial infarction"; *The New England journal of medicine 361*; pp. 868-877.
Klonoff, D. C. (2005) "Continuous Glucose Monitoring: Roadmap for 21st century diabetes therapy"; *Diabetes Care 28*; pp. 1231-1239.
Kohn, J.E. and Plaxco, K.W. (2005) "Engineering a signal transduction mechanism for protein-based biosensors"; *Proc. Natl. Acad. Sci. US.A. 102*; p. 10841-10845.
Koutsopoulos, S., et al; (2009) Controlled release of functional proteins through designer self-assembling peptide nanofiber hydrogel scaffold: *Proceedings of the National Academy of Sciences of the United States of America 106*; pp. 4623-4628.
Lanzavecchia et al.; (1987) "The use of hybrid hybridomas to target human cytotoxic T lymphocytes" *Eur. J Immunol. 17*, 105-111.

(56) References Cited

OTHER PUBLICATIONS

Lavigne, J. J. et al; (2001) "Sensing A Paradigm Shift in the Field of Molecular Recognition: From Selective to Differential Receptors"; *Angewandte Chemie International Edition 40*; pp. 3118-3130.

Le Cesne, A. et al; (2000) "Randomized phase III study comparing conventional-dose doxorubicin plus ifosfamide versus high-dose doxorubicin plus ifosfamide plus recombinant human granulocyte-macrophage colony-stimulating factor in advanced soft tissue sarcomas: A trial of the Europe."; *Journal of Clinical Oncology : Official Journal of the American Society of Clinical Oncology 18*; pp. 2676-2684.

Lee, M. O.; (1929) "Determination of the surface area of the white rat with its application to the expression of metabolic results"; *American Journal of Physiology—Legacy Content 89*; pp. 24-33.

McGregor, D. (2000) "Aminoglycosides"; *Kirk-Othmer Encyclopedia of Chemical Technology*; pp. 1-22; doi:10.1002/0471238961.0113091413030718.a01.

Medintz, I.L. and Deschamps, J.R. (2006) "Maltose-binding protein: a versatile platform for prototyping biosensing"; *Curr Opin Biotechnol. 7(1)*; pp. 17-27.

Oh, K.J. et al; (2009) "Beyond Molecular Beacons: Optical Sensors Based on the Binding-Induced Folding of Proteins and Polypeptides"; *Chem. Eur. J 15*; pp. 2244-2251.

Oiye, E. N., et al; (2009) "De Voltammetric determination of cocaine in confiscated samples using a cobalt hexacyanoferrate film-modified electrode"; *Forensic science international 192*; pp. 94-99.

Patolsky, F., et al; (2006) "Fabrication of silicon nanowire devices for ultrasensitive, label-free, real-time detection of biological and chemical species"; *Nature protocols 1*, pp. 1711-1724.

Plaxco, K. W. et al; (2010) "Switch-based biosensors: a new approach towards real-time, in vivo molecular detection"; *Trends in biotechnology 29*; pp. 1-5.

Rahman, A., et al; (1986). "Comparative pharmacokinetics of free doxorubicin and doxorubicin entrapped in cardiolipin liposomes"; *Cancer Research 46*; pp. 2295-2299.

Ramaley, L.; (1969) "Theory of square wave voltammetry"; *Analytical Chemistry 41(11)*; pp. 1362-1365.

Rand, P. W., et al; (1964) "Viscosity of Normal Human Blood Under Normothermic and Hypothermic Conditions"; *Journal of Applied Physiology 19*; pp. 117-122.

Rissin, D. M. et al; (2010) "Single-molecule enzyme-linked immunosorbent assay detects serum proteins at subfemtomolar concentrations"; *Nature biotechnology 28*; pp. 595-599.

Rowe et al.; "Reagentless Measurement of Aminoglycoside Antibiotics in Blood Serum via an Electrochemical, Ribonucleic Acid Aptamer-Based Biosensor"; *Anal Chem. 82(17)*; Sep. 1, 2010; pp. 7090-7095.

Shan et al.; "Plasmonic-based Imaging of Local Square Wave Voltammetry"; *Anal Chem. 83(19)*; (Oct. 2011) pp. 7394-7399.

Slack, S., et al; (1988) "Physicochemical and biochemical aspects of fibrinogen adsorption from plasma and binary protein solutions onto polyethylene and glass"; *Journal of Colloid and Interface Science 124*; pp. 535-551.

Stratton, M.M. et al. (2008) "A Ca2+—Sensing Molecular Switch Based on Alternate Frame Protein Folding," *ACS Chem. Biol. 3*, 723-732.

Swensen et al.; "Continuous, Real-Time Monitoring of Cocaine in Undiluted Blood Serum via a Microfluidic, Electrochemical Aptamer-Based Sensor"; *J Am Chem Soc. 131(12)*; Apr. 1, 2009; pp. 4262-4266.

Tremper, K. K. et al; (1989) "Pulse oximetry"; *Anesthesiology 70*; pp. 98-108.

Ueda, Y et al.; (1989) "Comparison of efficacy, toxicity and pharmacokinetics of free adriamycin and adriamycin linked to oxidized dextran in rats"; *Chemical& pharmaceutical bulletin 37*; pp. 1639-1641.

Uzawa, T., et al; (2010) "A mechanistic study of electron transfer from the distal termini of electrode-bound, single-stranded DNAs"; *Journal of the American Chemical Society 132*; pp. 16120-16126.

Valleebelisle, A. and Plaxo, K.W. (2010) "Structure-switching biosensors: inspired by Nature" *Curr. Opin. Struct. Biol. 20*; pp. 518-526.

Wang, J. (1999) "Amperometric biosensors for clinical and therapeutic drug monitoring: a review"; *Journal of pharmaceutical and biomedical analysis 19*; pp. 47-53.

Wilson, G. S. & Hu, Y.; (2000) "Enzyme-based biosensors for in vivo measurements"; *Chemical reviews 100*; pp. 2693-2704.

Wisniewski, N., et al; (2000) "Characterization of implantable biosensor membrane biofouling. Fresenius"; *Journal of Analytical Chemistry 366*; pp. 611-621.

Wochner, A. et al; (2008) "A DNA aptamer with high affinity and specificity for therapeutic anthracyclines"; *Analytical biochemistry 373*; pp. 34-42.

Xiao, Y. and Plaxco, K.W. (2009) "Electrochemical Approaches to Aptamer-Based Sensing". *In Functional Nucleic Acids for Sensing and Other Analytical Applications*(Lu, Y. and Li, Y., eds), pp. 179-198, New York,.

Yager, P. et al; (2006) "Microfluidic diagnostic technologies for global public health"; *Nature 442*; pp. 412-418.

Yamamoto, Y. et al: (1992) "A new strategy for the assessment of viable myocardium and regional myocardial blood flow using 15O-water and dynamic positron emission tomography"; *Circulation 86*; pp. 167-178.

Yoneyama, Y. et al; (2009) Wireless biosensor system for real-time cholesterol monitoring in fish "Nile tilapia"; *Talanta 80*; pp. 909-915.

Cruz-Toledo J, et al(2012) "Aptamer Base: a collaborative knowledge base to describe aptamers and SELEX experiments"; Database, vol. 2012, Article ID bas006, doi: 10.1093/database/bas006; pp. 1-8.

Lee, JF, et al(2004) "Aptamer Database"; Nucleic Acids Research, vol. 32, Database issue; pp. D95-D100.

\* cited by examiner

Panel A

Panel B

IN-VIVO MONITORING OF MOLECULAR TARGETS

CROSS-REFERENCE TO RELATED APPLICATIONS

This application is a 35 U.S.C. § 371 national stage of International Application No. PCT/US2014/013620, filed Jan. 29, 2014, which application claims the benefit of U.S. Provisional Application No. 61/784,130, filed Mar. 14, 2013, which applications are incorporated by reference herein in their entireties and for all purposes.

STATEMENT REGARDING FEDERALLY SPONSORED RESEARCH

The invention was made with Government support under Grant Nos. W911NF-09-D-001 and W911NF-10-2-0114 awarded by the U.S. Army Research Office (ARO), and Grant No. R01A1076899 awarded by the National Institute of Health (NIH). The government has certain rights in the invention.

INTRODUCTION

The continuous or semi-continuous, real-time measurement of specific target molecules circulating in vivo poses a variety of technological challenges. First, in order to measure in vivo concentrations in real time, a biosensor should be capable of directly analyzing patient fluids continuously or semi-continuously without discrete stages of sample preparation, batch processing or the addition of exogenous reagents. Second, the biosensor should achieve sufficient sensitivity, selectivity and dynamic range, in addition to the ability to resolve the fluctuations in biochemical analyte concentrations on their physiological time-scales. Finally, as prolonged exposure to whole blood and similar complex samples may expose the biosensor to blood cells and exogenous proteins that can disturb sensor readings, the biosensor should be capable of remaining stable in this environment with high signal-to-noise ratios (SNR) for extended periods of time. Because of these technological challenges, real-time measurements are currently only available for a very few analytes. For example, current measurement systems may exploit convenient properties of their targets such as the enzymatic oxidation of glucose (blood-glucose sensors) or absorbance shift in oxygenated hemoglobin (blood-oxygen sensor). However, these technologies are not easily applied to measure other analytes. Thus, there remains a need in the art for a system that can overcome each of these limitations for a wide range of clinically relevant analytes. The present disclosure addresses these issues and provides related advantages.

SUMMARY

The present disclosure provides devices, methods and systems for analyte detection and/or monitoring, e.g., the continuous and/or semi-continuous monitoring of in-vivo analyte concentrations in real time. Generally, the devices, methods and systems of the present disclosure make use of signaling probes; methods or devices for reducing interferent-based fouling of the signaling probes, non-specific binding to the signaling probes and/or occlusion of a sensor surface; and methods and/or devices for providing an adjusted signal based on a detected signal from the signaling probes. Compositions including conformation switching signaling probes are also provided.

Certain non-limiting aspects of the disclosure are provided below:

1. A method of determining an in vivo concentration of an analyte, the method including:
   continuously flowing a biological fluid from a living subject for a period of time;
   contacting the biological fluid or a component thereof with a signaling probe that produces a detectable signal based on specific binding of the signaling probe to the analyte when present in the biological fluid;
   detecting the detectable signal in response to a binding event between the analyte, when present in the biological fluid, and the signaling probe; reducing non-specific binding and/or fouling of the signaling probe by one or more components of the biological fluid; adjusting the detectable signal based on a background signal produced as a result of non-specific binding of the signaling probe to produce an adjusted signal; and determining an in vivo concentration of the analyte during the period of time based on the adjusted signal.

2. The method of 1, wherein the period of time is at least one hour.

3. The method of 1 or 2, wherein the signaling probe is a conformation switching probe.

4. The method of 3, wherein the conformation switching probe is a conformation switching aptamer.

5. The method of any one of 1-4, wherein the signaling probe includes a redox reporter.

6. The method of 5, wherein the redox reporter is selected from methylene blue, ferrocene and anthraquinone.

7. The method of 5 or 6, wherein the signaling probe is immobilized on an electrode.

8. The method of any one of 1-7, wherein the signaling probe is immobilized in a channel of a microfluidic device.

9. The method of any one of 1-8, wherein the microfluidic device includes a channel configured to receive a sample stream including the biological fluid and a buffer stream, and wherein the microfluidic device is further configured to provide a stacked laminar flow of the sample stream and buffer stream in the channel, when present in the microfluidic device.

10. The method of 9, wherein the stacked laminar flow is a vertically stacked laminar flow.

11. The method of 9, wherein the stacked laminar flow is a horizontally stacked laminar flow.

12. The method of any one of 1-11, wherein the biological fluid includes whole blood.

13. The method of 12, wherein the buffer stream includes an isotonic buffer.

14. The method of 9, wherein the height of the channel is from about 1 μm to about 1000 μm.

15. The method of 14, wherein the height of the channel is from about 100 μm to about 900 μm.

16. The method of 15, wherein the height of the channel is from about 200 μm to about 800 μm.

17. The method of 16, wherein the height of the channel is from about 300 μm to about 700 μm.

18. The method of 17, wherein the height of the channel is from about 400 μm to about 600 μm.

19. The method of 18, wherein the height of the channel is about 500 μm.

20. The method of 9, wherein the ratio of the thickness of the buffer stream to the height of the channel is from about 0.1:1 to about 1:1.

21. The method of 9, wherein the sample stream has a first flow rate, the buffer stream has a second flow rate, and the ratio of the second flow rate to the sum of the first and second flow rates is from about 0.1:1 to about 1:1.

22. The method of 21, wherein ratio of the second flow rate to the sum of the first and second flow rates is about 0.33:1.

23. The method of any one of 1-22, including administering a pharmacologically active agent based on the determined in vivo concentration of the analyte.

24. The method of any one of 1-23, including continuously or intermittently administering a pharmacologically active agent based on the determined in vivo concentration of the analyte over the period of time.

25. The method of 23 or 24, wherein the administering is via an infusion pump.

26. The method of any one of 23-25, wherein the administering is automatic.

27. The method of any one of 1-22, wherein the analyte is a pharmacologically active agent or a metabolite thereof, and the method includes:
   administering a pharmacologically active agent to the subject; and
   following the step of determining an in vivo concentration of the analyte,
   administering an adjusted dose of the pharmacologically active agent to the subject based on the determined in vivo concentration of the analyte.

28. A method of modulating an in vivo concentration of an analyte, the method including:
   continuously flowing a biological fluid from a living subject for a period of time;
   contacting the biological fluid or a component thereof with a signaling probe that produces a detectable signal based on specific binding of the signaling probe to the analyte when present in the biological fluid;
   detecting the detectable signal in response to a binding event between the analyte, when present in the biological fluid, and the signaling probe;
   reducing non-specific binding and/or fouling of the signaling probe by one or more components of the biological fluid;
   adjusting the detectable signal based on a background signal produced as a result of non-specific binding of the signaling probe to produce an adjusted signal;
   determining an in vivo concentration of the analyte during the period of time based on the adjusted signal; and
   continuously or intermittently administering a pharmacologically active agent based on the determined in vivo concentration of the analyte over the period of time,
   wherein the in vivo concentration of the analyte is modulated by the administering.

29. A method of administering a pharmacologically active agent, the method including:
   administering a pharmacologically active agent to a living subject;
   continuously flowing a biological fluid from the living subject for a period of time;
   contacting the biological fluid or a component thereof with a signaling probe that produces a detectable signal based on specific binding of the signaling probe to an analyte when present in the biological fluid, wherein the analyte is the pharmacologically active agent or a metabolite thereof;
   detecting the detectable signal in response to a binding event between the analyte, when present in the biological fluid, and the signaling probe; reducing non-specific binding and/or fouling of the signaling probe by one or more components of the biological fluid;
   adjusting the detectable signal based on a background signal produced as a result of non-specific binding of the signaling probe to produce an adjusted signal;
   determining an in vivo concentration of the analyte during the period of time based on the adjusted signal; and
   administering an adjusted dose of the pharmacologically active agent to the subject based on the determined in vivo concentration of the analyte.

30. A method of determining a concentration of an analyte in a sample fluid, the method including:
   flowing the sample fluid for a period of time;
   contacting the sample fluid or a component thereof with a signaling probe during the period of time, wherein the signaling probe produces a detectable signal based on specific binding of the signaling probe to the analyte when present in the sample fluid;
   detecting the detectable signal in response to a binding event between the analyte, when present in the sample fluid, and the signaling probe;
   reducing non-specific binding and/or fouling of the signaling probe by one or more components of the sample fluid;
   adjusting the detectable signal based on a background signal produced as a result of non-specific binding of the signaling probe to produce an adjusted signal; and
   determining the concentration of the analyte based on the adjusted signal.

31. The method of 30, wherein the sample fluid is an environmental sample.

32. The method of 30, wherein the sample fluid is a fluid produced by a biological or biochemical process.

33. The method of 30, wherein the sample fluid is a cell culture medium or cell culture supernatant.

34. A method of determining one or more pharmacokinetic parameters for a pharmacologically active agent, the method including:
   administering a pharmacologically active agent to a living subject;
   continuously flowing a biological fluid from the living subject for a period of time;
   contacting the biological fluid or a component thereof with a signaling probe that produces a detectable signal based on specific binding of the signaling probe to an analyte when present in the biological fluid, wherein the analyte is the pharmacologically active agent or a metabolite thereof;
   detecting the detectable signal in response to a binding event between the analyte, when present in the biological fluid, and the signaling probe;
   reducing non-specific binding and/or fouling of the signaling probe by one or more components of the biological fluid;
   adjusting the detectable signal based on a background signal produced as a result of non-specific binding of the signaling probe to produce an adjusted signal;
   determining an in vivo plasma concentration of the analyte during the period of time based on the adjusted signal; and
   determining one or more pharmacokinetic parameters for the pharmacologically active agent based on the determined in vivo plasma concentration of the analyte.

35. The method of 34, wherein the one or more pharmacokinetic parameters are selected from $C_{max}$, $C_{min}$, $C_{ss}$, $T_{max}$, $T_{1/2}$, AUC, Vd, bioavailability and clearance.

36. An analyte monitoring system including:
- means for continuously receiving a biological fluid from a living subject for a period of time;
- a signaling probe that produces a detectable signal based on specific binding of the signaling probe to an analyte when present in the biological fluid;
- means for reducing non-specific binding of the signaling probe by one or more components of the biological fluid; and
- a means for adjusting the detectable signal based on a background signal produced as a result of non-specific binding of the signaling probe to produce an adjusted signal, wherein the adjusted signal is indicative of an in vivo concentration of the analyte during the period of time.

37. The system of 36, wherein the period of time is at least one hour.

38. The system of 37, wherein the signaling probe is a conformation switching probe.

39. The system of 38, wherein the conformation switching probe is a conformation switching aptamer.

40. The system of any one of 36-39, wherein the conformation switching probe includes a redox reporter.

41. The system of 40, wherein the redox reporter is selected from methylene blue, ferrocene and anthraquinone.

42. The system of any one of 36-41, including means for administering a pharmacologically active agent based on the in vivo concentration of the analyte indicated by the adjusted signal.

43. The system of any one of 36-42, including means for continuously or intermittently administering a pharmacologically active agent based on the in vivo concentration of the analyte indicated by the adjusted signal over the period of time.

44. The system of 42 or 43, wherein the means for administering a pharmacologically active agent is a means for automatically administering the pharmacologically active agent.

45. An analyte monitoring system including:
- means for flowing a sample fluid for a period of time;
- a signaling probe configured to contact the sample fluid or a portion thereof during the period of time, wherein the signaling probe produces a detectable signal based on specific binding of the signaling probe to an analyte when present in the sample fluid;
- means for reducing non-specific binding of the signaling probe by one or more components of the sample fluid; and
- a means for adjusting the detectable signal based on a background signal produced as a result of non-specific binding of the signaling probe to produce an adjusted signal, wherein the adjusted signal is indicative of the concentration of the analyte in the sample fluid.

46. A system, including:
- a microfluidic device including a channel configured to receive a sample stream and a buffer stream, wherein the microfluidic device is further configured to provide a stacked laminar flow of the sample stream and buffer stream in the channel, when present in the microfluidic device; and
- a signaling probe that produces a detectable signal based on specific binding of the signaling probe to an analyte when present in the sample stream, wherein the signaling probe is positioned in the microfluidic device relative to the sample stream and the buffer stream, when present, so that the analyte, when present in the sample stream, is capable of selectively diffusing from the sample stream, through the buffer stream to contact the signaling probe; and
- means for detecting a signal from the signaling probe upon binding of the analyte to the signaling probe.

47. The system of 46, wherein the signaling probe is a conformation switching probe.

48. The system of 47, wherein the conformation switching probe is a conformation switching aptamer.

49. The system of any one of 46-48, wherein the stacked laminar flow is a vertically stacked laminar flow.

50. The system of any one of 46-48, wherein the stacked laminar flow is a horizontally stacked laminar flow.

51. The system of any one of 46-50, wherein the sample stream and the buffer stream are present in the microfluidic device.

52. The system of 51, wherein the sample stream includes whole blood.

53. The system of 52, wherein the buffer stream includes an isotonic buffer.

54. The system of any one of 46-53, wherein the height of the channel is from about 1 μm to about 1000 μm.

55. The system of 54, wherein the height of the channel is from about 100 μm to about 900 μm.

56. The system of 55, wherein the height of the channel is from about 200 μm to about 800 μm.

57. The system of 56, wherein the height of the channel is from about 300 μm to about 700 μm.

58. The system of 57, wherein the height of the channel is from about 400 μm to about 600 μm.

59. The system of 58, wherein the height of the channel is about 500 μm.

60. The system of any one of 51-59, wherein the ratio of the thickness of the buffer stream to the height of the channel is from about 0.1:1 to about 1:1.

61. The system of any one of 51-59, wherein the sample stream has a first flow rate, the buffer stream has a second flow rate, and the ratio of the second flow rate to the sum of the first and second flow rates is from about 0.1:1 to about 1:1.

62. The system of 61, wherein ratio of the second flow rate to the sum of the first and second flow rates is about 0.33:1.

63. The system of any one of 46-62, wherein the signaling probe includes a redox reporter.

64. The system of 63, wherein the redox reporter is selected from methylene blue, ferrocene and anthraquinone.

65. The system of 63 or 64, wherein the microfluidic device includes a first electrode and the signaling probe is immobilized on the first electrode.

66. The system of 65, wherein the signaling probe is a conformation switching probe which has a first conformation when not bound to the analyte and a second conformation when bound to the analyte, and wherein the second conformation positions the redox reporter closer to the electrode than the first conformation.

67. The system of 65 or 66, wherein the means for detecting a signal from the signaling probe is configured to detect a change in an electron transfer rate between the redox reporter and the electrode.

68. The system of any one of 46-67, wherein the means for detecting a signal from the signaling probe utilizes a differential measurement technique.

69. The system of 67, wherein signaling probe is a conformation switching probe and the means for detecting a signal from the signaling probe utilizes a differential measurement technique, wherein the differential measurement technique includes interrogating the electrode with a first square wave voltammetry (SWV) frequency to obtain a first signal and a second SWV frequency to obtain a second signal, taking the difference between the two signals, and dividing by the average of the two signals to obtain an adjusted signal.

70. The system of any one of 46-69, including means for continuously flowing the sample stream from a living organism to the channel.

71. The system of any one of 46-70, including a delivery device for administering a pharmacologically active agent based on the determined in vivo concentration of the analyte.

72. The system of 71, wherein the delivery device continuously or intermittently administers the pharmacologically active agent based on the determined in vivo concentration of the analyte over the period of time.

73. The system of 72, wherein the delivery device includes an infusion pump.

74. The system of 72 or 73, wherein the delivery device automatically administers the pharmacologically active agent based on the determined in vivo concentration of the analyte over the period of time.

75. A method of determining the concentration of an analyte in a sample, the method including:
contacting the sample or a component thereof with a conformation switching aptamer with specific binding affinity for the analyte, wherein the conformation switching aptamer is immobilized on an electrode and includes a redox reporter, and wherein the conformation switching aptamer has a first conformation when not bound to the analyte and a second conformation when bound to the analyte, and the second conformation positions the redox reporter closer to the electrode than the first conformation;
detecting a conformation change in the conformation switching aptamer upon binding of the analyte, when present, to the conformation switching aptamer, wherein said detecting includes voltammetrically interrogating the electrode to obtain a first signal and a second signal, and combining the first and second signal via a mathematical operation to obtain an adjusted signal; and
determining the concentration of the analyte in the sample from the adjusted signal.

76. The method of 75, wherein the voltammetrically interrogating utilizes alternating current voltammetry, linear sweep voltammetry, or differential pulse voltammetry to obtain the first signal and the second signal.

77. The method of 75, wherein the voltammetrically interrogating includes interrogating the electrode with a first square wave voltammetry (SWV) frequency to obtain the first signal and a second SWV frequency to obtain the second signal.

78. The method of any one of 75-77, wherein the mathematical operation includes a mathematical operation selected from a ratio, a difference, and a difference squared divided by a sum squared.

79. The method of any one of 75-77, wherein the mathematical operation includes taking the difference between the two signals, and dividing by the average of the two signals.

80. The method of any one of 75-79, wherein the redox reporter is selected from methylene blue, ferrocene and anthraquinone.

81. The method of any one of 75-80, wherein the contacting occurs in a microfluidic device, the microfluidic device including a channel including a sample stream and a buffer stream, wherein the sample stream includes the sample, wherein the microfluidic device provides a stacked laminar flow of the sample stream and buffer stream in the channel, and wherein the buffer stream is positioned between the electrode and the sample stream so that the analyte, when present in the sample, is capable of selectively diffusing from the sample stream, through the buffer stream to contact the conformation switching aptamer.

82. The method of 81, wherein the stacked laminar flow is a vertically stacked laminar flow.

83. The method of 81, wherein the stacked laminar flow is a horizontally stacked laminar flow.

84. The method of any one of 81-83, wherein the sample stream includes whole blood.

85. The method of 84, wherein the buffer stream includes an isotonic buffer.

86. The method of any one of 81-85, wherein the height of the channel is from about 1 µm to about 1000 µm.

87. The method of 86, wherein the height of the channel is from about 100 µm to about 900 µm.

88. The method of 87, wherein the height of the channel is from about 200 µm to about 800 µm.

89. The method of 88, wherein the height of the channel is from about 300 µm to about 700 µm.

90. The method of 89, wherein the height of the channel is from about 400 µm to about 600 µm.

91. The method of 90, wherein the height of the channel is about 500 µm.

92. The method of any one of 81-92, wherein the ratio of the thickness of the buffer stream to the height of the channel is from about 0.1:1 to about 1:1.

93. The method of any one of 81-92, wherein the sample stream has a first flow rate, the buffer stream has a second flow rate, and the ratio of the second flow rate to the sum of the first and second flow rates is from about 0.1:1 to about 1:1.

94. The method of 93, wherein ratio of the second flow rate to the sum of the first and second flow rates is about 0.33:1.

95. The method of any one of 75-94, wherein the method includes continuously receiving the sample from a living organism and continuously determining the concentration of the analyte in the sample for a period of at least 2 hours.

96. The method of 95, wherein the period is at least 4 hours.

97. The method of 96, wherein the period is at least 8 hours.

98. The method of 97, wherein the period is at least 12 hours.

99. The method of 98, wherein the period is at least 24 hours.

100. The method of any one of 75-99, wherein the analyte is a pharmacologically active agent or a metabolite thereof, and the method includes:
administering a pharmacologically active agent to the subject;
receiving the sample from the subject; and
following the step of determining an in vivo concentration of the analyte, administering an adjusted dose of the pharmacologically active agent to the subject based on the determined concentration of the analyte.

101. A differential measurement method, including:
voltammetrically interrogating an electrode to obtain a first signal and a second signal; and combining the first and second signal via a mathematical operation to obtain an adjusted signal, wherein the electrode includes immobilized thereon a conformation switching aptamer with specific binding affinity for an analyte, the conformation switching aptamer including an redox reporter, wherein the conformation switching aptamer has a first conformation when not bound to the analyte and a second conformation when bound to the analyte, and the second conformation positions the redox reporter closer to the electrode than the first conformation.

102. The method of 101, wherein the voltammetrically interrogating utilizes alternating current voltammetry, linear sweep voltammetry, or differential pulse voltammetry to obtain the first signal and the second signal.

103. The method of 101, wherein the voltammetrically interrogating includes interrogating the electrode with a first square wave voltammetry (SWV) frequency to obtain the first signal and a second SWV frequency to obtain the second signal.

104. The method of any one of 101-103, wherein the mathematical operation includes a mathematical operation selected from a ratio, a difference, and a difference squared divided by a sum squared.

105. The method of any one of 101-103, wherein the mathematical operation includes taking the difference between the two signals, and dividing by the average of the two signals.

106. The method of 101, wherein the redox reporter is selected from methylene blue, ferrocene and anthraquinone.

107. A microfluidic device including
a channel configured to receive a sample stream and a buffer stream, wherein the microfluidic device is further configured to provide a stacked laminar flow of the sample stream and buffer stream in the channel, when present in the microfluidic device; and
a signaling probe that produces a detectable signal based on specific binding of the signaling probe to an analyte when present in the sample stream, wherein the signaling probe is positioned in the microfluidic device relative to the sample stream and the buffer stream, when present in the microfluidic device, so that the analyte, when present in the sample stream, is capable of selectively diffusing from the sample stream, through the buffer stream to contact the signaling probe.

108. The microfluidic device of 107, wherein the signaling probe is a conformation switching probe.

109. The microfluidic device of 108, wherein the conformation switching probe is a conformation switching aptamer.

110. The microfluidic device of any one of 107-109, wherein the stacked laminar flow is a vertically stacked laminar flow.

111. The microfluidic device of any one of 107-109, wherein the stacked laminar flow is a horizontally stacked laminar flow.

112. The microfluidic device of any one of 107-111, wherein the sample stream and the buffer stream are present in the microfluidic device.

113. The microfluidic device of 112, wherein the sample stream includes whole blood.

114. The microfluidic device of 113, wherein the buffer stream includes an isotonic buffer.

115. The microfluidic device of any one of 107-114, wherein the height of the channel is from about 1 µm to about 1000 µm.

116. The microfluidic device of 115, wherein the height of the channel is from about 100 µm to about 900 µm.

117. The microfluidic device of 116, wherein the height of the channel is from about 200 µm to about 800 µm.

118. The microfluidic device of 117, wherein the height of the channel is from about 300 µm to about 700 µm.

119. The microfluidic device of 118, wherein the height of the channel is from about 400 µm to about 600 µm.

120. The microfluidic device of 119, wherein the height of the channel is about 500 µm.

121. The microfluidic device of any one of 112-121, wherein the ratio of the thickness of the buffer stream to the height of the channel is from about 0.1:1 to about 1:1.

122. The microfluidic device of any one of 112-121, wherein the sample stream has a first flow rate, the buffer stream has a second flow rate, and the ratio of the second flow rate to the sum of the first and second flow rates is from about 0.1:1 to about 1:1.

123. The microfluidic device of 122, wherein ratio of the second flow rate to the sum of the first and second flow rates is about 0.33:1.

124. The microfluidic device of any one of 107-123, wherein the signaling probe includes a redox reporter.

125. The microfluidic device of 124, wherein the redox reporter is selected from methylene blue, ferrocene and anthraquinone.

126. The microfluidic device of 124 or 125, wherein the microfluidic device includes a first electrode and the signaling probe is immobilized on the first electrode.

127. The microfluidic device of 126, wherein the signaling probe is a conformation switching probe having a first conformation when not bound to the analyte and a second conformation when bound to the analyte, and wherein the second conformation positions the redox reporter closer to the electrode than the first conformation.

128. A kanamycin-binding aptamer including a DNA sequence having at least 90% sequence identity with the DNA sequence set forth in SEQ ID NO: 2.

129. The kanamycin-binding aptamer of 128, wherein the kanamycin-binding aptamer includes a redox reporter bound thereto.

130. The kanamycin-binding aptamer of 128 or 129, wherein the kanamycin-binding aptamer is immobilized on a support.

131. A doxorubicin-binding aptamer including a DNA sequence having at least 90% sequence identity with the DNA sequence set forth in SEQ ID NO: 1.

132. The doxorubicin-binding aptamer of 131, wherein the doxorubicin-binding aptamer includes a redox reporter bound thereto.

133. The doxorubicin-binding aptamer of 131 or 132, wherein doxorubicin-binding aptamer is immobilized on a support.

BRIEF DESCRIPTION OF THE DRAWINGS

The foregoing summary, as well as the following detailed description of the disclosure, will be better understood when read in conjunction with the appended figures. For the purpose of illustrating the disclosure, shown in the figures are certain embodiments. It should be understood, however, that the disclosure is not limited to the precise arrangements, examples and instrumentalities shown.

DEFINITIONS

Figure 1:
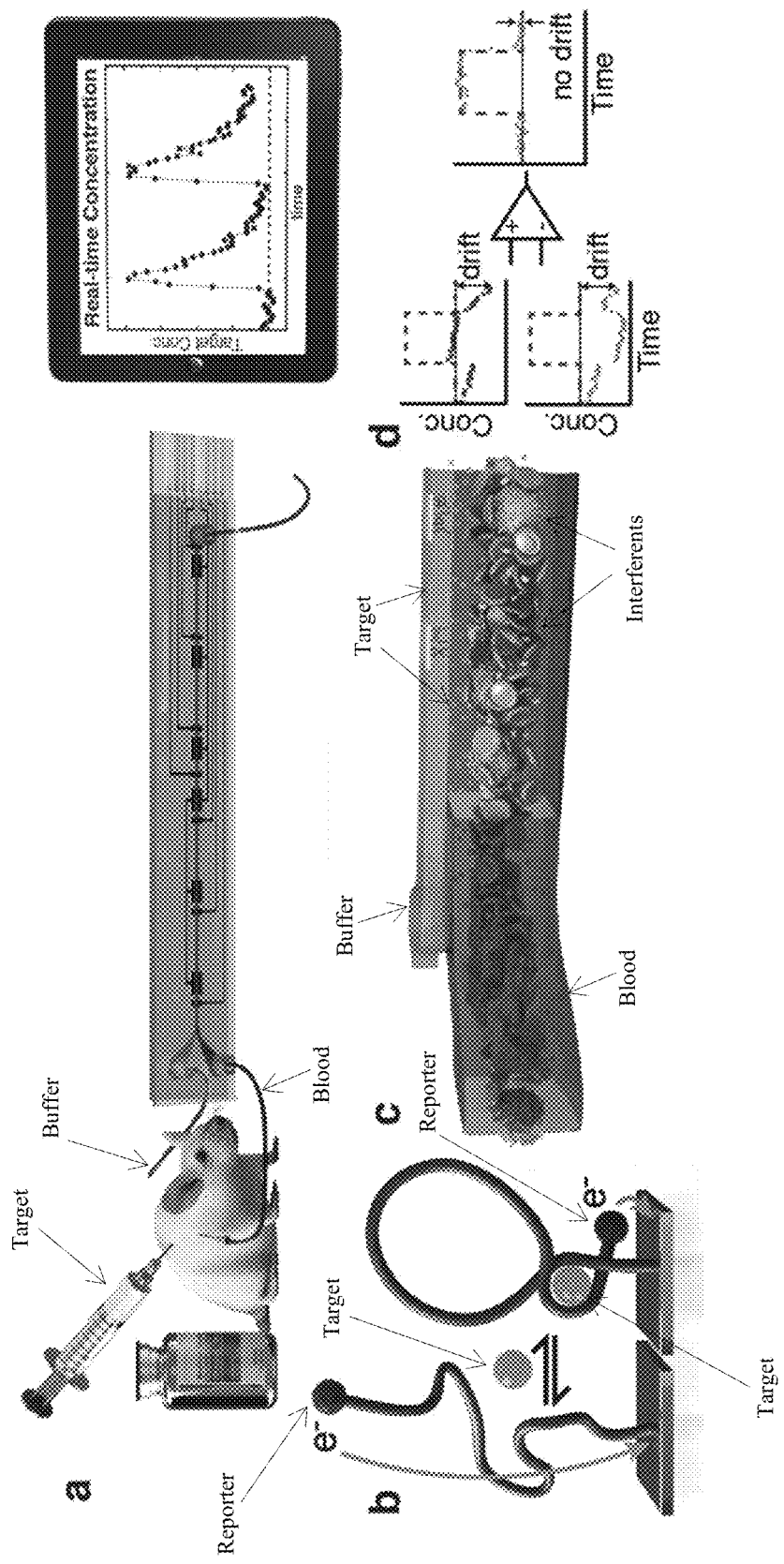
FIG. 1 provides an overview of an embodiment of a Microfluidic Electrochemical Detector for In vivo Continuous monitoring (MEDIC) system according to the present disclosure. (a) MEDIC achieves continuous, quantitative measurement of specific molecular analyte concentrations in the blood of living animals. (b) When the target binds the aptamer probe, the rate of electron transfer between the methylene blue reporter and a microfabricated electrode increases, yielding a measureable current change. (c) The continuous diffusion filter (CDF), formed by vertically stacked laminar flow of buffer and blood, selectively permits transport of the target to the sensor while excluding interferents. (d) Kinetic differential measurement (KDM) improves detection by minimizing drift and enhancing SNR.

As used herein, the term "signaling probe" refers to a binding agent or a group of binding agents which report a detectable signal indicative of a specific binding interaction with a target, e.g., a target analyte.

As used herein, the term "conformation switching probe" refers to a probe, e.g., an aptamer probe, capable of specifically binding a target, wherein the conformation switching probe has a first conformation when bound to the target and a second conformation when not bound to the target, and wherein one or both of the first conformation and the second conformation provides a detectable signal. Conformation switching probes may be reversible or non-reversible as described herein.

As used herein the term "aptamer" or "aptamer sequence" refers to a nucleic acid having a specific binding affinity for a target, e.g., a target molecule, wherein such target is other than a polynucleotide that binds to the aptamer or aptamer sequence through a mechanism which predominantly depends on Watson/Crick base pairing.

The terms "nucleic acid", "nucleic acid sequence", "nucleic acid molecule" and "polynucleotide" may be used interchangeably herein and refer to a polymeric form of nucleotides of any length, either deoxyribonucleotides or ribonucleotides, or analogs thereof, and may include naturally occurring nucleotides and/or modified nucleotides. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

The terms "peptide", "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The term "sequence" as used, for example, in the context of an aptamer sequence, a nucleic acid sequence or an amino acid sequence may refer to the primary structure, e.g., the order of monomeric subunits, e.g., nucleotides or amino acids, and/or to the molecule having the primary structure.

The terms "antibody" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins including an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. Also encompassed by the terms are Fab', Fv, F(ab')$_2$, and other antibody fragments that retain specific binding to antigen.

Antibodies may exist in a variety of other forms including, for example, Fv, Fab, and (Fab')$_2$, as well as bi-functional (i.e. bi-specific) hybrid antibodies (e.g., Lanzavecchia et al., *Eur. J. Immunol.* 17, 105 (1987)) and in single chains (e.g., Huston et al., *Proc. Natl. Acad. Sci. U.S.A.*, 85, 5879-5883 (1988) and Bird et al., Science, 242, 423-426 (1988), which are incorporated herein by reference). (See, generally, Hood et al., *Immunology*, Benjamin, N.Y., 2nd ed. (1984), and Hunkapiller and Hood, *Nature*, 323, 15-16 (1986).

The terms "label" and "detectable label" may be used interchangeably herein to refer to a molecule capable of detection, including, but not limited to, radioactive isotopes; redox reporters; luminescers, e.g., bioluminescers, chemiluminescers, electroluminescers, and photoluminescers, e.g., fluorescers; chromophores; enzymes; enzyme substrates; enzyme cofactors; enzyme inhibitors; dyes; metal ions; metal sols; ligands (e.g., biotin, avidin, strepavidin or haptens) and the like. Exemplary detectable moieties suitable for use as detectable labels include affinity tags and fluorescent proteins.

As used herein, the term "redox reporter" refers to a molecule which exhibits a reversible change in oxidation state at specific electrode potentials (e.g. methylene blue or ferrocene).

The term "fluorescer" refers to a substance or a portion thereof which is capable of exhibiting fluorescence in the detectable range.

The term "affinity tag" is used herein to denote a peptide segment that can be attached to a target that can be detected using a molecule that binds the affinity tag and provides a detectable signal (e.g., a fluorescent compound or protein). In principal, any peptide or protein for which an antibody or other specific binding agent is available can be used as an affinity tag.

"Stringency conditions" refers to conditions in a reaction mixture that influence formation of complexes between candidate nucleic acid agents, e.g., aptamer sequences, and a target. Additional stringency conditions are described, for example, in U.S. Application Publication No. 2009/0170718, the disclosure of which is incorporated by reference herein in its entirety and for all purposes.

The terms "specific binding," "specifically bind," and the like, refer to the ability of a first binding molecule or moiety to preferentially bind (covalently or non-covalently) to a second binding molecule or moiety relative to other molecules or moieties in a reaction mixture.

As used herein, a "member of a specific binding pair" is a member of a specific binding pair interaction. It should be noted that when either member of the binding pair is referred to as the first member, the remaining member is understood to be the second member and vice versa. Examples of specific binding pair interactions include immune binding interactions such as antigen/antibody and hapten/antibody as well as non-immune binding interactions such as complementary nucleic acid binding, biotin/avidin and biotin/streptavidin.

As used herein, the terms "determining," "measuring," "assessing," and "assaying" are used interchangeably and include both quantitative and qualitative determinations unless the context clearly indicates otherwise.

As used interchangeably herein, the terms "active agent", "pharmacologically active agent" and "beneficial agent" refer to any substance intended for use in the diagnosis, cure, mitigation, treatment, or prevention of any disease, disorder, or condition or intended to affect the structure or function of the body, other than food. It can include any beneficial agent or substance that is biologically active or meant to alter animal physiology.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a conformation switching probe" includes a plurality of such conformation switching probes and reference to "the microfluidic device" includes reference to one or more microfluidic devices and equivalents thereof known to those skilled in the art, and so forth. It is further noted that the claims may be drafted to exclude any element, e.g., any optional element. As such, this statement is intended to serve as antecedent basis for use of such exclusive terminology as "solely," "only" and the like in connection with the recitation of claim elements, or use of a "negative" limitation.

To the extent any part of the disclosure, including the definition or usage of any term herein, conflicts with the description in an application or reference incorporated by reference herein, the instant application shall control.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. This is intended to provide support for all such combinations.

DETAILED DESCRIPTION

The present disclosure provides devices, methods and systems for analyte detection and/or monitoring, e.g., the continuous and/or semi-continuous monitoring of in-vivo analyte concentrations in real time. Generally, the devices, methods and systems of the present disclosure make use of signaling probes; methods or devices for reducing interferent-based fouling of the signaling probes, non-specific binding to the signaling probes and/or occlusion of a sensor surface; and methods and/or devices for providing an adjusted signal based on a detected signal from the signaling probes. Compositions including conformation switching signaling probes are also provided.

The devices, methods and systems of the present disclosure facilitate continuous and/or semi-continuous monitoring of analyte levels in real time, and may be used in connection with known medication delivery devices to provide analyte-responsive drug delivery systems, including open- and closed-loop systems. Accordingly, in some embodiments the devices, methods and systems of the present disclosure may facilitate direct control of in vivo concentrations of therapeutics in response to ongoing metabolic changes in a subject, thereby allowing for dose optimization based on individual subject response.

The devices, methods and systems of the present disclosure also facilitate detection and/or monitoring of a variety of samples, including, e.g., detection and/or monitoring of environmental samples, detection and/or monitoring of one or more industrial processes, and detection and/or monitoring of excreted biomarkers from cell systems.

Signaling Probes

The disclosed methods, devices and systems make use of signaling probes. Signaling probes effectively translate a specific binding interaction with a target into a detectable signal. Suitable signaling probes include, for example:

1) a binding agent which is capable of specifically binding the target, wherein the presence of the specific binding interaction is signaled via an inherent property of the target itself, e.g., the target's mass, index of refraction, absorption, and the like;

2) a combination of a capture binding agent and a reporter binding agent, wherein the capture binding agent is capable of specifically binding to the target at a first location on the target and the reporter binding agent is capable of specifically binding to the target at a second location on the target, and wherein the reporter binding agent includes a detectable label;

3) a reversible conformation switching probe, wherein the presence of a specific binding interaction between the reversible conformation switching probe and the target is signaled by a conformation change in the probe which modulates a property of a detectable label, e.g., location, accessibility, or motion of the detectable label; and 4) a non-reversible conformation switching probe, wherein the non-reversible conformation switching probe is initially in a first conformation which conformation changes to a second conformation upon specific binding of the non-reversible conformation switching probe to the target, and wherein the presence of the specific binding interaction between the non-reversible conformation switching probe and the target is signaled by releasing a detectable label, enabling binding of a detectable label, or catalysis.

Binding agents which may be used as signaling probes include, e.g., nucleic acid binding agents, e.g., aptamers, and polypeptide binding agents, e.g., antibodies, as described herein.

Suitable detectable labels which may be used in connection with signaling probes include, e.g., magnetic particles, radioactive isotopes; redox reporters; surface-enhanced Raman scattering (SERS) reporter molecules; luminescers, e.g., bioluminescers, chemiluminescers, electroluminescers, and photoluminescers, e.g., fluorescers.

Conformation switching probes which may be used in connection with the disclosed devices, methods and systems create a direct link between a detectable signal and an analyte binding event. A variety of conformation switching probes known in the art may be utilized in connection with the disclosed devices, methods and systems. In addition, new conformation switching probes are disclosed herein.

Examples of known conformation switching probes include naturally occurring biomolecular switches which may be used to detect either their natural ligands or new molecular targets created via the rational or selection-driven re-design of their binding sites. Examples include the two-domain periplasmic-binding-protein superfamily, which undergo a binding-induced conformational change and may be used to detect a wide range of specific sugars, amino acids, and inorganic ions. See, e.g., K. W. Plaxco, H. T. Soh (2011) *Trends Biotechnol.* 29:1, pp. 1-5; Vallee-Belisle, A. and Plaxo, K. W. (2010) *Curr. Opin. Struct. Biol.* 20, 518-526; and Medintz, I. L. and Deschamps, J. R. (2006) *Curr. Opin. Struct. Biol.* 17, 17-27; the disclosures of each of which are incorporated by reference herein.

Examples of proteins which may be suitable for use as conformation switching probes include members of the periplasmic-binding protein superfamily such as glucose-binding protein, maltose-binding protein, ribose-binding protein, arabinose-binding protein, histidine-binding protein, glutamine-binding protein. Additional examples include periplasmic binding proteins of *E. coli* and engineered versions thereof, as are all homologues, analogues and/or paralogues of members of this superfamily. Other examples include hexokinase, phosphofructokinase, DNA polymerase, etc.

Examples of known non-naturally occurring, conformation switching probes include polypeptides, proteins and aptamers, e.g., DNA or RNA aptamers, which have been engineered to undergo a large-scale conformation change upon analyte binding. See, for example, Oh, K. J. et al. (2009) *Chem. Eur. J.* 15, 2244-2251; Kohn, J. E. and Plaxco, K. W. (2005) *Proc. Natl. Acad. Sci. U.S.A* 102, 10841-10845; Stratton, M. M. et al. (2008) *ACS Chem. Biol.* 3, 723-732; Xiao, Y. and Plaxco, K. W. (2009) Electrochemical aptamer sensors. *In Functional Nucleic Acids for Sensing and Other Analytical Applications* (Lu, Y. and Li, Y., eds), pp. 179-198, New York, Springer; the disclosure of each of which is incorporated by reference herein. Aptamers can be engineered to undergo a large-scale conformation change upon target binding, e.g., by destabilization, which couples binding to a change in the folding equilibrium constant, or by introduction of a short auxiliary sequence complementary to the aptamer, which forces it to undergo a double-stranded-to-aptamer fold transition upon target binding.

Conformation switching aptamers directed against a number of specific proteins, inorganic ions and small molecules have been described. See, for example, Xiao, Y. and Plaxco, K. W. (2009) Electrochemical aptamer sensors. *In Functional Nucleic Acids for Sensing and Other Analytical Applications* (Lu, Y. and Li, Y., eds), pp. 179-198, New York, Springer; and Lubin, A. A. and Plaxco, K. W. (2010) *Acc. Chem. Res.* 43, 496-505; the disclosure of each of which is incorporated by reference herein.

As discussed above, conformation switching probes which may be used in connection with the disclosed devices, methods and systems create a direct link between a detectable signal and an analyte binding event. The signal may be provided by a variety of detectable labels, which may be incorporated into the conformation switching probes, e.g., at a 3' or 5' end of a conformation switching aptamer. Suitable detectable labels may include, e.g., magnetic particles, radioactive isotopes; redox reporters; surface-enhanced Raman scattering (SERS) reporter molecules; luminescers, e.g., bioluminescers, chemiluminescers, electroluminescers, and photoluminescers, e.g., fluorescers.

Where a redox reporter is selected as the detectable label for a signaling probe, e.g., a conformation switching probe, the redox reporter can be a redox-active metal center or a redox-active organic molecule. It can be a natural organic cofactor such as NAD, NADP, FAD or a natural metal center such as Blue Copper, iron-sulfur clusters, or heme, or a synthetic center such as an organometallic compound such as a ruthenium complex, or organic ligand such as a quinone.

The redox reporter can be a metal-containing group (e.g., a transition metal-containing group) that is capable of reversibly or semi-reversibly transferring one or more electrons. A number of possible transition metal-containing redox reporters can be used. In some embodiments, the reporter group has a functional group suitable for covalent coupling to the conformation switching probe (e.g., thiol-reactive functionalities such as maleimides or iodoacetamide for coupling to unique cysteine residues in a protein). The reporter group can be capable of undergoing an amperometric or potentiometric change in response to ligand binding. Suitable transition metals for use in the invention include, but are not limited to, copper (Cu), cobalt (Co), palladium (Pd), iron (Fe), ruthenium (Ru), rhodium (Rh), osmium (Os), rhenium (Re), platinum (Pt), scandium (Sc), titanium (Ti), vanadium (V), chromium (Cr), manganese (Mn), nickel (Ni), molybdenum (Mo), technetium (Tc), tungsten (W), and iridium (Ir). In some embodiments, suitable metals are selected from ruthenium, osmium, iron, platinum and palladium.

In some embodiments, the redox reporter is selected from ferrocene, methylene blue and anthraquinone.

The redox reporter can be bound covalently or non-covalently to a signaling probe, e.g., conformation switching probe, e.g., at a 3' or 5' end of a conformation switching aptamer. Where the signaling probe is a protein, the redox reporter can be present in the signaling probe as a covalent conjugate with the protein or it can be a metal center that forms part of the protein matrix (for instance, a redox center such as iron-sulfur clusters, heme, Blue copper, the electrochemical properties of which are sensitive to its local environment). Alternatively, the redox reporter can be present as a fusion between the protein and a metal binding domain (for instance, a small redox-active protein such as a cytochrome). In some embodiments, the redox reporter is covalently conjugated to a protein signaling probe via a maleimide functional group bound to a cysteine (thiol) on the protein.

A variety of signal readouts may be utilized depending on the nature of the detectable label selected. For example, where a redox reporter is used, an electrochemical output based on the binding-induced change in redox rates may be utilized. Additional readouts include binding induced change in fluorescence, luminesce, electrochemiluminescence, Surface Plasmon Resonance, or Surface Enhanced Raman Spectroscopy.

The signaling probe, e.g., a conformation switching probe, may be immobilized on one or more surfaces in the context of the disclosed devices, methods and systems, e.g., to provide a sensor structure. For example, where an electrochemical based output is utilized a signaling probe, e.g., a conformation switching probe, may be immobilized, e.g., at one end, to (or in proximity to) a conductive electrode surface to provide a sensor structure. Suitable conductive materials, which may be utilized for the conductive electrode surface, include gold, silver, copper, aluminum, platinum, iridium, palladium, rhodium, mercury, silicon, osmium, ruthenium, gallium arsenide, indium phosphide, mercury, cadmium telluride, carbon and the like. In some embodiments, the conductive material is selected from gold, silver, aluminum foil, and doped silicon wafers.

The signaling probes, e.g., conformation switching probes, may be immobilized on the one or more surfaces via any of a variety of methods known in the art, including, e.g, thiolation to facilitate self-assembly of nucleic acid signaling probes onto gold working electrodes. In some embodiments, the signaling probes, e.g., conformation switching probes, may be bound to the one or more surfaces via a self-assembled monolayer which includes molecules that can bind or interact with a metal, metal oxide, glass, quartz or modified polymer surface in order to form a chemisorbed monolayer. Molecules making up self-assembled monolayers can include a functional group that adheres to the surface layer and further can include a pendant moiety that can interact with a molecule to be anchored above the self-assembled monolayer.

Methods, Devices and Systems for Reducing Non-Specific Binding

As discussed above, one aspect of the present disclosure relates to methods, devices and systems for reducing interferent-based fouling of signaling probes, non-specific binding to signaling probes and/or occlusion of a sensor surface. This may be important, for example, in in vivo monitoring applications where the analyte may be present in a complex sample such as whole blood which contains a variety of interferents which can result in fouling and/or non-specific binding of the signaling probes or occlusion of the sensor surface. This problem may be exacerbated where the monitoring is continuous or semi continuous over an extended period of time.

One suitable system for reducing interferent-based fouling of the signaling probes, non-specific binding to the signaling probes and/or occlusion of a sensor surface is described herein as a continuous diffusion filter (CDF). The CDF involves stacked laminar flows, e.g., vertically or horizontally stacked laminar flows, of a buffer stream and a sample stream, which may be provided in the context of a microfluidic device configured to receive the buffer stream and sample stream. The streams are configured, and the signaling probes are positioned, such that the analyte can selectively diffuse from the sample stream, through the buffer stream, to contact the signaling probes, while interferents, e.g., blood cells, are selectively repressed from reaching signaling probes due to their lower diffusivity. This system exploits the differences in diffusivity between the analyte and the interferents.

As discussed in the Examples below, CDF thickness and analyte residence time may be adjustable by controlling the total flow and the ratio of the two flow rates such that the analyte selectively diffuses across the buffer stream relative to the interferents. Accordingly, CDFs capable of excluding a variety of interferents based on their relative diffusivities are readily achievable.

Another suitable system for reducing interferent-based fouling of the signaling probes, non-specific binding to the signaling probes and/or occlusion of a sensor surface may be accomplished by providing a nanochannel parallel to a sample stream, wherein the nanochannel is sized to allow entry of the analyte or analytes of interest from the sample stream while excluding larger interferents, e.g., blood cells. The nanochannel may be sized such that it is no wider 1000 nm, e.g., no wider than 500 nm, or no wider than 100 nm. By positioning the nanochannel parallel to the flow of the sample stream, blockage of the nanochannel can be prevented. By positioning the signaling probes in the nanochannel, or with the nanochannel otherwise in between the probes and the sample stream, selective access to the probes by the analyte may be achieved.

Similar exclusion of larger interferents in the sample stream can be achieved by positioning a hydrogel, e.g., a hydrogel having a pore size of 1000 nm or less (e.g., 500 nm or less, or 100 nm or less), between the probes and the sample stream. To prevent blockage of the hydrogel pores, the hydrogel may be provided parallel to the sample stream flow.

Interferents could also be prevented from contacting the signaling probes by applying a repulsive force directly to the interferents. Such repulsive forces may include, e.g., acoustophoretic forces, Dean forces or dielectrophoretic forces. For example, to exclude large interferents such as platelets and blood cells, forces could be applied up steam of the electrodes to continuously direct the large interferents away from the sensing surface while retaining the smaller targets.

This could be accomplished through inertial and Dean forces, via the inclusion of a curved segment of the microchannel, or via acoustophoretic separation via the inclusion of piezoelectric oscillation at a wavelength equal to the channel height which could direct blood cells toward the pressure node in the center of the channel and away from the surface. By way of example, translation of a 5 μm particle, a distance of 1 μm from the channel wall, could be performed by applying a force of at least 0.1 pN for 0.1 s.

Methods for Providing an Adjusted Signal

As discussed above, one aspect of the present disclosure relates to methods, devices and systems for providing an adjusted signal based on a detected signal from a signaling probe. This may be accomplished, for example, by obtaining a first signal and a second signal from a signaling probe, and combining the first and second signal via a mathematical operation to obtain an adjusted signal. In some embodiments, the first and second signals are obtained by voltametrically interrogating an electrode as described herein. The step of voltammetrically interrogating the electrode may utilize alternating current voltammetry, linear sweep voltammetry, or differential pulse voltammetry to obtain the first signal and the second signal. The mathematical operation may include, e.g., a mathematical operation selected from a ratio, a difference, and a difference squared divided by a sum squared.

One suitable method, which allows for correction of signal drift, is described herein as kinetic differential measurement (KDM). As discussed in the Examples below, KDM is a process that exploits the frequency-dependent behavior of a single probe to allow it function as both the sensor and reference signal for baseline-correction. This can be achieved by modulating the interrogation frequencies to obtain both a "signal on" and "signal off" signal. These signals can then be differentially combined, e.g., by taking the difference between the two signals and dividing by the average of the two signals, to provide a signal adjusted for background.

While the Examples below demonstrate KDM based on modulating frequencies, similar results can also be achieved by modulating the amplitude of the interrogation waveform. Signal correction can also be performed by utilizing a non-participating reference probe, e.g., immobilized on the same sensor device but with a label that yields a separate signal (e.g. fluorophores with different emission wavelengths or redox reporters with different redox potentials), or by immobilizing these on an independently-addressable sensor surface. A non-participating sensor can act as a control that does not recognize the target molecules but otherwise behave similarly. Non-participating aptamer sensors could be selected, for example, through negative selection, as non-binders.

Microfluidic Devices and Methods of Making Same

The present disclosure provides microfluidic devices which find use, for example, in the disclosed methods and systems. In some embodiments, a microfluidic device according to the present disclosure includes at least a first channel configured to receive a sample stream and a buffer stream, wherein the microfluidic device is further configured to provide a stacked laminar flow of the sample stream and buffer stream in the channel. In some embodiments, such a microfluidic device includes a signaling probe as described herein, e.g., a conformation switching probe as described herein, that produces a detectable signal based on specific binding of the signaling probe to an analyte when present in the sample stream. The signaling probe may be positioned in the microfluidic device relative to the sample stream and the buffer stream so that the analyte, when present in the sample stream, is capable of selectively diffusing from the sample stream, through the buffer stream to contact the signaling probe. This structure and probe configuration can effectively reduce interferent-based fouling of the signaling probes and/or non-specific binding to the signaling probes or occlusion of the sensor surface.

Additional microfluidic device/signaling probe configurations are described herein and may be utilized to reduce interferent-based fouling of the signaling probes, non-specific binding to the signaling probes, and/or occlusion of a sensor surface.

Where a stacked laminar flow of the sample stream and buffer stream are provided, the stacked laminar flow may be a vertically stacked laminar flow or a horizontally stacked laminar flow.

In some embodiments, the height of the channel configured to receive the sample stream and buffer stream may be from about 1 μm to about 1000 μm, e.g., from about 1 μm to about 900 μm, from about 1 μm to about 800 μm, from about 1 μm to about 700 μm, from about 1 μm to about 600 μm, from about 1 μm to about 500 μm, from about 1 μm to about 400 μm, from about 1 μm to about 300 μm, from about 1 μm to about 200 μm, from about 1 μm to about 100 μm, from about 1 μm to about 50 μm, from about 1 μm to about 10 μm, or from about 1 μm to about 5 μm.

In some embodiments, the height of the channel configured to receive the sample stream and buffer stream may be from about 100 μm to about 900 μm, e.g., from about 200 μm to about 800 μm, from about 300 μm to about 700 μm, from about 400 μm to about 600 μm, or about 500 μm.

In some embodiments, a microfluidic device according to the present disclosure may be configured such that the ratio of the thickness of the buffer stream to the height of the channel is from about 0.1:1 to about 1:1, e.g., from about 0.2:1 to about 1:1, from about 0.3:1 to about 1:1, from about 0.4:1 to about 1:1, from about 0.5:1 to about 1:1, from about 0.6:1 to about 1:1, from about 0.7:1 to about 1:1, from about 0.8:1 to about 1:1, or from about 0.9:1 to about 1:1. In some embodiments, the ratio of the thickness of the buffer stream to the height of the channel is from about 0.1:1 to about 0.2:1, from about 0.2:1 to about 0.3:1, from about 0.3:1 to about 0.4:1, from about 0.4:1 to about 0.5:1, from about 0.5:1 to about 0.6:1, from about 0.6:1 to about 0.7:1, from about 0.7:1 to about 0.8:1, or from about 0.8:1 to about 0.9:1.

In some embodiments, during operation of the microfluidic device, the sample stream has a first flow rate, the buffer stream has a second flow rate, and the ratio of the second flow rate to the sum of the first and second flow rates is from about 0.1:1 to about 1:1, e.g., from about 0.2:1 to about 1:1, from about 0.3:1 to about 1:1, from about 0.4:1 to about 1:1, from about 0.5:1 to about 1:1, from about 0.6:1 to about 1:1, from about 0.7:1 to about 1:1, from about 0.8:1 to about 1:1, or from about 0.9:1 to about 1:1. In some embodiments, the ratio of the second flow rate to the sum of the first and second flow rates is from about 0.1:1 to about 0.2:1, from about 0.2:1 to about 0.3:1, from about 0.3:1 to about 0.4:1, from about 0.4:1 to about 0.5:1, from about 0.5:1 to about 0.6:1, from about 0.6:1 to about 0.7:1, from about 0.7:1 to about 0.8:1, or from about 0.8:1 to about 0.9:1.

Microfluidics devices according to the present disclosure may be characterized in various ways. In certain embodiments, for example, microfluidics devices have at least one "micro" channel. Such channels may have at least one cross-sectional dimension on the order of a millimeter or smaller (e.g., less than or equal to about 1 millimeter). For certain applications, this dimension may be adjusted; in some embodiments the at least one cross-sectional dimension is about 500 micrometers or less. In some embodiments, again as applications permit, the cross-sectional dimension is about 100 micrometers or less (or even about 10 micrometers or less—sometimes even about 1 micrometer or less). A cross-sectional dimension is one that is generally perpendicular to the direction of centerline flow, although it should be understood that when encountering flow through elbows or other features that tend to change flow direction, the cross-sectional dimension in play need not be strictly perpendicular to flow. It should also be understood that in some embodiments, a micro-channel may have two or more cross-sectional dimensions such as the height and width of a rectangular cross-section or the major and minor axes of an elliptical cross-section. Either of these dimensions may be compared against sizes presented here.

In some embodiments, microfluidic devices according to the present disclosure are fabricated using microfabrication technology. Such technology is commonly employed to fabricate integrated circuits (ICs), microelectromechanical devices (MEMS), display devices, and the like. Among the types of microfabrication processes that can be employed to produce small dimension patterns in microfluidic device fabrication are photolithography (including X-ray lithography, e-beam lithography, etc.), self-aligned deposition and etching technologies, anisotropic deposition and etching processes, self-assembling mask formation (e.g., forming layers of hydrophobic-hydrophilic copolymers), etc.

In view of the above, it should be understood that some of the principles and design features described herein can be scaled to larger devices and systems including devices and systems employing channels reaching the millimeter or even centimeter scale channel cross-sections. Thus, when describing some devices and systems as "microfluidic," it is intended that the description apply equally, in certain embodiments, to some larger scale devices.

When referring to a microfluidic "device" it is generally intended to represent a single entity in which one or more channels, reservoirs, stations, etc. share a continuous substrate, which may or may not be monolithic. A microfluidics "system" may include one or more microfluidic devices and associated fluidic connections, electrical connections, control/logic features, etc. Aspects of microfluidic devices include the presence of one or more fluid flow paths, e.g., channels, having dimensions as discussed herein.

In certain embodiments, microfluidic devices according to the present disclosure provide a continuous flow of a fluid medium, which may include an analyte of interest. Fluid flowing through a channel in a microfluidic device exhibits many interesting properties. Typically, the dimensionless Reynolds number is extremely low, resulting in flow that always remains laminar. Further, in this regime, two fluids joining will not easily mix, and diffusion alone may drive the mixing of two compounds.

Various features and examples of microfluidic device components suitable for use with in connection with the disclosed microfluidic devices will now be described.

Substrate

Substrates used in microfluidic systems are the supports in which the necessary elements for fluid transport are provided. The basic structure may be monolithic, laminated, or otherwise sectioned. Commonly, substrates include one or more microchannels serving as conduits for samples and reagents (if necessary). They may also include input ports, output ports, and/or features to assist in flow control.

In certain embodiments, the substrate choice may be dependent on the application and design of the device. Substrate materials are generally chosen for their compatibility with a variety of operating conditions. Limitations in microfabrication processes for a given material are also relevant considerations in choosing a suitable substrate. Useful substrate materials include, e.g., glass, polymers, silicon, metal, and ceramics.

Polymers are standard materials for microfluidic devices because they are amenable to both cost effective and high volume production. Polymers can be classified into three categories according to their molding behavior: thermoplastic polymers, elastomeric polymers and duroplastic polymers. Thermoplastic polymers can be molded into shapes above the glass transition temperature, and will retain these shapes after cooling below the glass transition temperature. Elastomeric polymers can be stretched upon application of an external force, but will go back to original state once the external force is removed. Elastomers do not melt before reaching their decomposition temperatures. Duroplastic polymers have to be cast into their final shape because they soften a little before the temperature reaches their decomposition temperature.

Among the polymers that may be used in microfabricated devices according to the present disclosure are polydimethylsiloxane (PDMS), polyamide (PA), polybutylenterephthalate (PBT), polycarbonate (PC), polyethylene (PE), polymethylmethacrylate (PMMA), polyoxymethylene (POM), polypropylene (PP), polyphenylenether (PPE), polystyrene (PS) and polysulphone (PSU). The chemical and physical properties of polymers can limit their uses in microfluidics devices. Specifically in comparison to glass, the lower resistance against chemicals, the aging, the mechanical stability, and the UV stability can limit the use of polymers for certain applications.

Glass, which may also be used as the substrate material, has specific advantages under certain operating conditions. Since glass is chemically inert to most liquids and gases, it is particularly appropriate for applications employing certain solvents that have a tendency to dissolve plastics. Additionally, its transparent properties make glass particularly useful for optical or UV detection.

Methods of Fabrication

Microfabrication processes differ depending on the type of materials used in the substrate and the desired production volume. For small volume production or prototypes, fabrication techniques include LIGA, powder blasting, laser ablation, mechanical machining, electrical discharge machining, photoforming, etc. Technologies for mass production of microfluidic devices may use either lithographic or master-based replication processes. Lithographic processes for fabricating substrates from silicon/glass include both wet and dry etching techniques commonly used in fabrication of semiconductor devices. Injection molding and hot embossing typically are used for mass production of plastic substrates.

Glass, Silicon and Other "Hard" Materials (Lithography, Etching, Deposition)

The combination of lithography, etching and deposition techniques may be used to make microcanals and microcavities out of glass, silicon and other "hard" materials. Technologies based on the above techniques are commonly applied in for fabrication of devices in the scale of 0.1-500 micrometers.

Microfabrication techniques based on current semiconductor fabrication processes are generally carried out in a clean room. The quality of the clean room is classified by the number of particles <4 µm in size in a cubic inch. Typical clean room classes for MEMS microfabrication are 1000 to 10000.

In certain embodiments, photolithography may be used in microfabrication. In photolithography, a photoresist that has been deposited on a substrate is exposed to a light source through an optical mask. Conventional photoresist methods allow structural heights of up to 10-40 µm. If higher structures are needed, thicker photoresists such as SU-8, or polyimide, which results in heights of up to 1 mm, can be used.

After transferring the pattern on the mask to the photoresist-covered substrate, the substrate is then etched using either a wet or dry process. In wet etching, the substrate—area not protected by the mask—is subjected to chemical attack in the liquid phase. The liquid reagent used in the etching process depends on whether the etching is isotropic or anisotropic. Isotropic etching generally uses an acid to form three-dimensional structures such as spherical cavities in glass or silicon. Anisotropic etching forms flat surfaces such as wells and canals using a highly basic solvent. Wet anisotropic etching on silicon creates an oblique channel profile.

Dry etching involves attacking the substrate by ions in either a gaseous or plasma phase. Dry etching techniques can be used to create rectangular channel cross-sections and arbitrary channel pathways. Various types of dry etching that may be employed including physical, chemical, physico-chemical (e.g., RIE), and physico-chemical with inhibitor. Physical etching uses ions accelerated through an electric field to bombard the substrate's surface to "etch" the structures. Chemical etching may employ an electric field to migrate chemical species to the substrate's surface. The chemical species then reacts with the substrate's surface to produce voids and a volatile species.

In certain embodiments, deposition is used in microfabrication. Deposition techniques can be used to create layers of metals, insulators, semiconductors, polymers, proteins and other organic substances. Most deposition techniques fall into one of two main categories: physical vapor deposition (PVD) and chemical vapor deposition (CVD). In one approach to PVD, a substrate target is contacted with a holding gas (which may be produced by evaporation for example). Certain species in the gas adsorb to the target's surface, forming a layer constituting the deposit. In another approach commonly used in the microelectronics fabrication industry, a target containing the material to be deposited is sputtered with using an argon ion beam or other appropriately energetic source. The sputtered material then deposits on the surface of the microfluidic device. In CVD, species in contact with the target react with the surface, forming components that are chemically bonded to the object. Other deposition techniques include: spin coating, plasma spraying, plasma polymerization, dip coating, casting and Langmuir-Blodgett film deposition. In plasma spraying, a fine powder containing particles of up to 100 µm in diameter is suspended in a carrier gas. The mixture containing the particles is accelerated through a plasma jet and heated. Molten particles splatter onto a substrate and freeze to form a dense coating. Plasma polymerization produces polymer films (e.g. PMMA) from plasma containing organic vapors.

Once the microchannels, microcavities and other features have been etched into the glass or silicon substrate, the etched features may be sealed to ensure that the microfluidic device is "watertight." When sealing, adhesion can be applied on all surfaces brought into contact with one another. The sealing process may involve fusion techniques such as those developed for bonding between glass-silicon, glass-glass, or silicon-silicon.

Anodic bonding can be used for bonding glass to silicon. A voltage is applied between the glass and silicon and the temperature of the system is elevated to induce the sealing of the surfaces. The electric field and elevated temperature induces the migration of sodium ions in the glass to the glass-silicon interface. The sodium ions in the glass-silicon interface are highly reactive with the silicon surface forming a solid chemical bond between the surfaces. The type of glass used should ideally have a thermal expansion coefficient near that of silicon (e.g. Pyrex Corning 7740).

Fusion bonding can be used for glass-glass or silicon-silicon sealing. The substrates are first forced and aligned together by applying a high contact force. Once in contact, atomic attraction forces (primarily van der Waals forces) hold the substrates together so they can be placed into a furnace and annealed at high temperatures. Depending on the material, temperatures used ranges between about 600 and 1100° C.

Polymers/Plastics

A number of techniques may be employed for micromachining plastic substrates in accordance with embodiments disclosed in the present disclosure. Among these are laser ablation, stereolithography, oxygen plasma etching, particle jet ablation, and microelectro-erosion. Some of these techniques can be used to shape other materials (glass, silicon, ceramics, etc.) as well.

To produce multiple copies of a microfluidic device, replication techniques are employed. Such techniques involve first fabricating a master or mold insert containing the pattern to be replicated. The master is then used to mass-produce polymer substrates through polymer replication processes.

In the replication process, the master pattern contained in a mold is replicated onto the polymer structure. In certain embodiments, a polymer and curing agent mix is poured onto a mold under high temperatures. After cooling the mix, the polymer contains the pattern of the mold, and is then removed from the mold. Alternatively, the plastic can be injected into a structure containing a mold insert. In micro-injection, plastic heated to a liquid state is injected into a mold. After separation and cooling, the plastic retains the mold's shape.

PDMS (polydimethylsiloxane), a silicon-based organic polymer, may be employed in the molding process to form microfluidic structures. Because of its elastic character, PDMS is well suited for microchannels between about 5 and 500 µm. Specific properties of PDMS make it particularly suitable for microfluidic purposes:

1) It is optically clear which allows for visualization of the flows;
2) PDMS when mixed with a proper amount of reticulating agent has elastomeric qualities that facilitates keeping microfluidic connections "watertight;"
3) Valves and pumps using membranes can be made with PDMS because of its elasticity;
4) Untreated PDMS is hydrophobic, and becomes temporarily hydrophilic after oxidation of surface by oxygen plasma or after immersion in strong base; oxidized PDMS adheres by itself to glass, silicon, or polyethylene, as long as those surfaces were themselves exposed to an oxygen plasma.
5) PDMS is permeable to gas. Filling of the channel with liquids is facilitated even when there are air bubbles in the canal because the air bubbles are forced out of the material. But it's also permeable to non polar-organic solvents.

Microinjection can be used to form plastic substrates employed in a wide range of microfluidic designs. In this process, a liquid plastic material is first injected into a mold under vacuum and pressure, at a temperature greater than the glass transition temperature of the plastic. The plastic is then cooled below the glass transition temperature. After removing the mold, the resulting plastic structure is the negative of the mold's pattern.

Yet another replicating technique is hot embossing, in which a polymer substrate and a master are heated above the polymer's glass transition temperature, Tg (which for PMMA or PC is around 100-180° C.). The embossing master is then pressed against the substrate with a preset compression force. The system is then cooled below Tg and the mold and substrate are then separated.

Typically, the polymer is subjected to the highest physical forces upon separation from the mold tool, particularly when the microstructure contains high aspect ratios and vertical walls. To avoid damage to the polymer microstructure, material properties of the substrate and the mold tool may be taken into consideration. These properties include: sidewall roughness, sidewall angles, chemical interface between embossing master and substrate and temperature coefficients. High sidewall roughness of the embossing tool can damage the polymer microstructure since roughness contributes to frictional forces between the tool and the structure during the separation process. The microstructure may be destroyed if frictional forces are larger than the local tensile strength of the polymer. Friction between the tool and the substrate may be important in microstructures with vertical walls. The chemical interface between the master and substrate could also be of concern. Because the embossing process subjects the system to elevated temperatures, chemical bonds could form in the master-substrate interface. These interfacial bonds could interfere with the separation process. Differences in the thermal expansion coefficients of the tool and the substrate could create addition frictional forces.

Various techniques can be employed to form molds, embossing masters, and other masters containing patterns used to replicate plastic structures through the replication processes mentioned above. Examples of such techniques include LIGA (described below), ablation techniques, and various other mechanical machining techniques. Similar techniques can also be used for creating masks, prototypes and microfluidic structures in small volumes. Materials used for the mold tool include metals, metal alloys, silicon and other hard materials.

Laser ablation may be employed to form microstructures either directly on the substrate or through the use of a mask. This technique uses a precision-guided laser, typically with wavelength between infrared and ultraviolet. Laser ablation may be performed on glass and metal substrates, as well as on polymer substrates. Laser ablation can be performed either through moving the substrate surface relative to a fixed laser beam, or moving the beam relative to a fixed substrate. Various micro-wells, canals, and high aspect structures can be made with laser ablation.

Certain materials such as stainless steel make very durable mold inserts and can be micromachined to form structures down to the 10-μm range. Various other micromachining techniques for microfabrication exist including μ-Electro Discharge Machining (μ-EDM), μ-milling, focused ion beam milling. μ-EDM allows the fabrication of 3-dimensional structures in conducting materials. In μ-EDM, material is removed by high-frequency electric discharge generated between an electrode (cathode tool) and a workpiece (anode). Both the workpiece and the tool are submerged in a dielectric fluid. This technique produces a comparatively rougher surface but offers flexibility in terms of materials and geometries.

Electroplating may be employed for making a replication mold tool/master out of, e.g., a nickel alloy. The process starts with a photolithography step where a photoresist is used to defined structures for electroplating. Areas to be electroplated are free of resist. For structures with high aspect ratios and low roughness requirements, LIGA can be used to produce electroplating forms. LIGA is a German acronym for Lithographic (Lithography), Galvanoformung (electroplating), Abformung (molding). In one approach to LIGA, thick PMMA layers are exposed to x-rays from a synchrotron source. Surfaces created by LIGA have low roughness (around 10 nm RMS) and the resulting nickel tool has good surface chemistry for most polymers.

As with glass and silicon devices, polymeric microfluidic devices may be sealed before they become functional. Lamination is one method used to seal plastic microfluidic devices. In one lamination process, a PET foil (about 30 μm) coated with a melting adhesive layer (typically 5-10 μm) is rolled with a heated roller, onto the microstructure. Through this process, the lid foil is sealed onto the channel plate. Several research groups have reported a bonding by polymerization at interfaces, whereby the structures are heated and force is applied on opposite sides to close the channel. But excessive force applied may damage the microstructures. Both reversible and irreversible bonding techniques exist for plastic-plastic and plastic-glass interfaces. One method of reversible sealing involves first thoroughly rinsing a PDMS substrate and a glass plate (or a second piece of PDMS) with methanol and bringing the surfaces into contact with one another prior to drying. The microstructure is then dried in an oven at 65° C. for 10 min. No clean room is required for this process. Irreversible sealing is accomplished by first thoroughly rinsing the pieces with methanol and then drying them separately with a nitrogen stream. The two pieces are then placed in an air plasma cleaner and oxidized at high power for about 45 seconds. The substrates are then brought into contact with each other and an irreversible seal forms spontaneously.

Other available techniques include laser and ultrasonic welding. In laser welding, polymers are joined together through laser-generated heat. This method has been used in the fabrication of micropumps. Ultrasonic welding is another bonding technique that may be employed in some applications.

Figure 2:
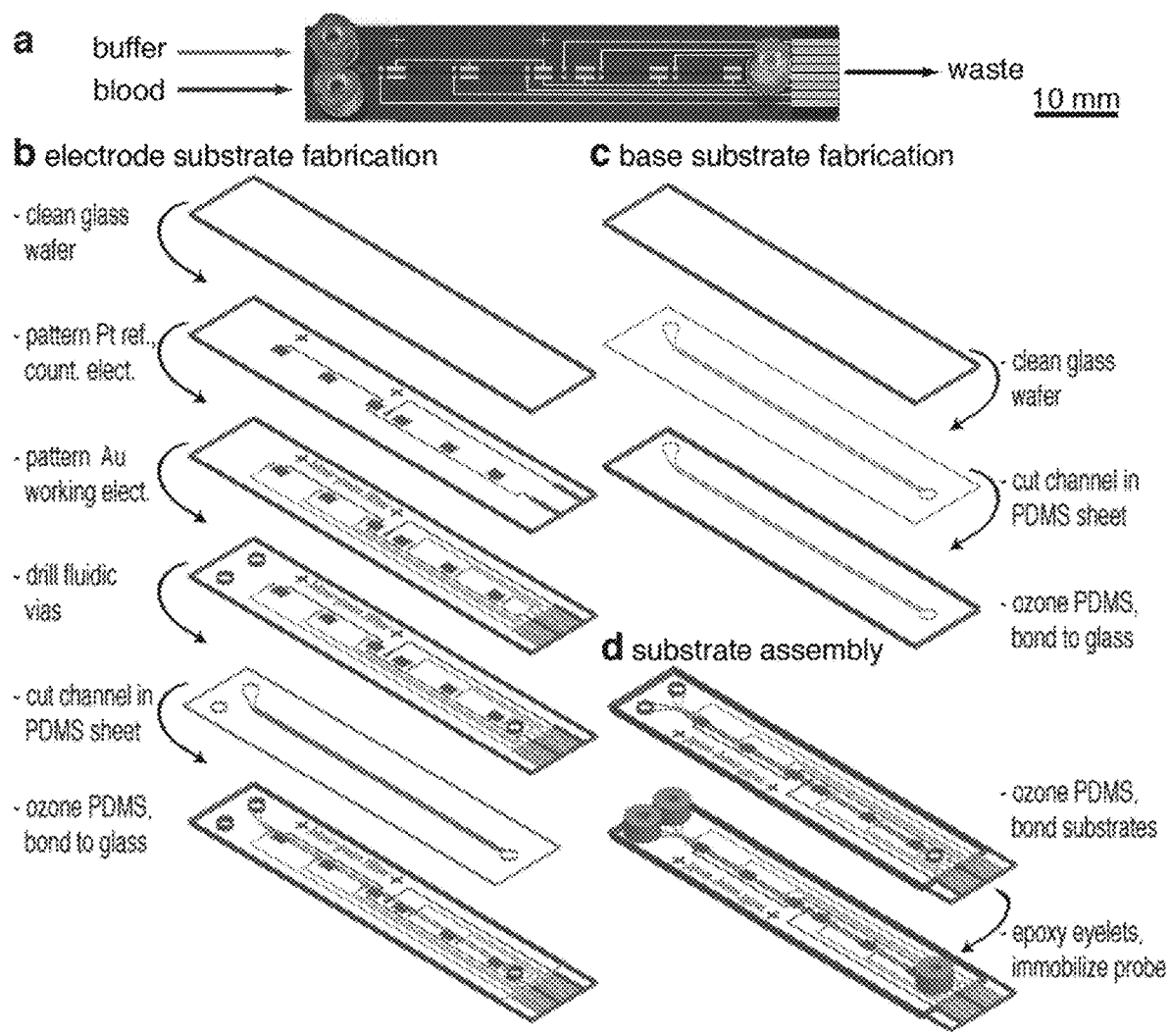
FIG. 2 shows the device architecture and general fabrication scheme for an embodiment of a MEDIC device according to the present disclosure. (a) Optical micrograph of the MEDIC chip. The MEDIC device is constructed of two stacked PDMS channels sandwiched between glass substrates, one of which bears sensing electrodes. The central channel is 40 mm long with a square cross-section of 500 µm×500 µm. Probes are immobilized on a set of six gold working electrodes (surface area=0.25 mm2), interdigitated with counter and reference electrodes to form an electrochemical cell. The device is fabricated in three phases. (b) Electrodes are patterned on a glass substrate, which is then drilled for vias, and bonded to an ozone-treated PDMS sheet bearing the upper channel. (c) The lower channel is cut into a PDMS sheet, treated with ozone and bonded to the base glass substrate. (d) The two remaining exposed PDMS surfaces are ozone treated, aligned and bonded together. Fluidic ports are epoxied to the surface above the vias. The chip is then subjected to the probe immobilization protocol and ready for use.

An exemplary microfluidic device fabrication method is described in the materials and methods for Examples 1-5 and is depicted generally in FIG. 2.

Methods of Detecting, Monitoring and/or Administering

The disclosed devices and systems facilitate a variety of detection and/or monitoring methods, e.g., detection and/or monitoring, e.g., in vivo detection and/or monitoring, of whole blood or other biological fluids for an analyte of interest, e.g., a drug or drug metabolite; detection and/or monitoring of environmental samples, e.g., waste water, drinking water, run-off, etc., for an analyte of interest; detection and/or monitoring of one or more industrial processes, e.g., by detection and/or monitoring of a product or byproduct of the industrial process or processes, e.g., bioreactor monitoring; and detection and/or monitoring of excreted biomarkers from cell systems, e.g., cell culture excretions, such as stem-cell culture excretions; among others.

Accordingly, in some embodiments, the present disclosure provides methods of determining an in vivo concentration of an analyte. In some embodiments, such a method includes: continuously flowing a biological fluid from a living subject for a period of time; contacting the biological fluid or a component thereof with a signaling probe that produces a detectable signal based on specific binding of the signaling probe to the analyte when present in the biological fluid; detecting the detectable signal in response to a binding event between the analyte, when present in the biological fluid, and the signaling probe; reducing non-specific binding and/or fouling of the signaling probe by one or more components of the biological fluid; adjusting the detectable signal based on a background signal produced as a result of non-specific binding of the signaling probe to produce an adjusted signal; and determining an in vivo concentration of the analyte during the period of time based on the adjusted signal.

In some embodiments, methods of modulating an in vivo concentration of an analyte are provided. In some embodiments, such a method includes: continuously flowing a biological fluid from a living subject for a period of time; contacting the biological fluid or a component thereof with a signaling probe that produces a detectable signal based on specific binding of the signaling probe to the analyte when present in the biological fluid; detecting the detectable signal in response to a binding event between the analyte, when present in the biological fluid, and the signaling probe; reducing non-specific binding and/or fouling of the signaling probe by one or more components of the biological fluid; adjusting the detectable signal based on a background signal produced as a result of non-specific binding of the signaling probe to produce an adjusted signal; determining an in vivo concentration of the analyte during the period of time based on the adjusted signal; and continuously or intermittently administering a pharmacologically active agent based on the determined in vivo concentration of the analyte over the period of time, wherein the in vivo concentration of the analyte is modulated by the administering.

In some embodiments, methods of administering a pharmacologically active agent are provided. In some embodiments, such a method includes: administering a pharmacologically active agent to a living subject; continuously flowing a biological fluid from the living subject for a period of time; contacting the biological fluid or a component thereof with a signaling probe that produces a detectable signal based on specific binding of the signaling probe to an analyte when present in the biological fluid, wherein the analyte is the pharmacologically active agent or a metabolite thereof; detecting the detectable signal in response to a binding event between the analyte, when present in the biological fluid, and the signaling probe; reducing non-specific binding and/or fouling of the signaling probe by one or more components of the biological fluid; adjusting the detectable signal based on a background signal produced as a result of non-specific binding of the signaling probe to produce an adjusted signal; determining an in vivo concentration of the analyte during the period of time based on the adjusted signal; and administering an adjusted dose of the pharmacologically active agent to the subject based on the determined in vivo concentration of the analyte.

In some embodiments, methods of determining a concentration of an analyte in a sample fluid are provided. Suitable sample fluids may include, e.g., an environmental sample fluid, a fluid produced by a biological or biochemical process, and a cell culture medium or cell culture supernatant. In some embodiments, such a method includes: flowing the sample fluid for a period of time; contacting the sample fluid or a component thereof with a signaling probe during the period of time, wherein the signaling probe produces a detectable signal based on specific binding of the signaling probe to the analyte when present in the sample fluid; detecting the detectable signal in response to a binding event between the analyte, when present in the sample fluid, and the signaling probe; reducing non-specific binding and/or fouling of the signaling probe by one or more components of the sample fluid; adjusting the detectable signal based on a background signal produced as a result of non-specific binding of the signaling probe to produce an adjusted signal; and determining the concentration of the analyte based on the adjusted signal.

In some embodiments, methods of determining one or more pharmacokinetic parameters for a pharmacologically active agent are provided. In some embodiments, such a method includes: administering a pharmacologically active agent to a living subject; continuously flowing a biological fluid from the living subject for a period of time; contacting the biological fluid or a component thereof with a signaling probe that produces a detectable signal based on specific binding of the signaling probe to an analyte when present in the biological fluid, wherein the analyte is the pharmacologically active agent or a metabolite thereof; detecting the detectable signal in response to a binding event between the analyte, when present in the biological fluid, and the signaling probe; reducing non-specific binding and/or fouling of the signaling probe by one or more components of the biological fluid; adjusting the detectable signal based on a background signal produced as a result of non-specific binding of the signaling probe to produce an adjusted signal; determining an in vivo plasma concentration of the analyte during the period of time based on the adjusted signal; and determining one or more pharmacokinetic parameters for the pharmacologically active agent based on the determined in vivo plasma concentration of the analyte. The one or more pharmacokinetic parameters may be selected from, e.g., $C_{max}$, $C_{min}$, $C_{ss}$, $T_{max}$, $T_{1/2}$, AUC, Vd, bioavailability and clearance of the pharmacologically active.

Analytes

The disclosed methods, devices and systems may be applied to the detection and/or measurement of a range of molecules having varying molecular weights. This can be accomplished by adjusting the stringency of the methods, devices and systems for reducing interferent-based fouling of the signaling probes, non-specific binding to the signaling probes and/or occlusion of the sensor surface, e.g., by adjusting the stringency of the CDF described herein. For example, the Examples below demonstrate that for small molecules a continuous diffusion filter of 125 μm and a residence time (molecule transit time before passing an electrode) of ~30 seconds provided sufficient target transport and non-target rejection. For lower diffusivity molecules such as procalcitonin (MW=13 kDa) or thrombin (MW=36 kDa), the diffusion layer can be decreased and/or the residence time increased as necessary to accomplish efficient capture of the analyte of interest while rejecting interferents.

Accordingly, analytes which may be detected and/or monitored according to the disclosed methods, devices and systems may include, for example, small molecule drugs, e.g., those having a molecular weight of less than 800 Daltons, and metabolites thereof; and environmental toxins, e.g., polychlorinated biphenyls (PCBs), pesticides, fungal toxins, phthalates, volatile organic compounds (VOCs), dioxins, asbestos, and heavy metals (e.g., arsenic, mercury, lead, aluminum and cadmium).

Other Sample Fluids and Extraction Modes

The disclosed methods, devices and systems have been successfully demonstrated with respect to whole blood, the most complex human fluid. However, the disclosed methods, devices and systems could be adapted to measure a variety of other human fluids including urine, intraperitoneal fluid, interstitial fluid, cerebral spinal fluid, lymph, saliva and tears, as well as cell culture media and any fluids containing soluble analytes or excreted biomarkers, including samples for process control and environmental monitoring.

In the Examples discussed below, the sample was drawn from subjects via a catheter. Such a method could be similarly employed to draw other fluids. Additionally, for subcutaneous measurement a perfusion system could be employed to flow a carrier fluid into an internal region and collect sample through a microdialysis tube, which would serve as the device input.

Re-Circulation

The disclosed methods, systems and devices may also be utilized to return the monitored biological fluid to a subject from whom it was withdrawn. In such embodiments, an inline pump could be utilized (such as a peristaltic pump). Where the buffer employed is isotonic and is flowed at a fraction of the sample flow rate (e.g., ~1:4), the dilutive impact on the sample would be minimal. However, if the dilution was substantial, a second output port could be added which owing to laminar flow, would re-circulate the sample portion of the stacked output. Such a configuration would allow for applications with the following constraints: higher-flow rate requirements and/or low total sample volume (e.g., intraperitoneal fluid).

Semi-Continuous Configuration

While the disclosed methods, devices and systems facilitate continuous monitoring, such methods, devices and systems could also operate in a semi-continuous manner over longer time scales (days, weeks or months), to enable long life while resolving physiological events over this time scale. For example, to monitor Amphotericin B, an antifungal treatment (which has a biphasic half-life of 24 hours and 15 days in the initial and second phase respectively), a measurement may be required only once every hour. In this case, a device according to the present disclosure could cycle through a period of activity and dormancy. During a brief active period, the device could operate normally to measure the target concentration. During the longer dormant period, buffer could be flushed through the system with no sample injection. In this configuration, a special wash buffer (such as guanidine hydrochloride) could be utilized to restore the sensor to its initial state, to preserve lifetime or enable use of slow-off rate affinity agents, or employ a control sample for ratiometric measurement.

Simultaneous Monitoring

The methods, devices and systems of the present disclosure can support multiple affinity agents, e.g., located on multiple electrodes, to examine a range of biomarkers. This could include, e.g., a drug, and its metabolites (such as chemotherapeutic methotrexate, and its metabolite 4-amino-4-deoxy-N-methylpteroic) or biomarkers that are indicative of the disease (such as Carcinoembryonic Antigen for cancer) or the impact of the treatment (such a creatinine indicating kidney function).

Feedback Control

By monitoring the levels of specific drugs, metabolites, or biomarkers using the disclosed methods, devices and systems, it is possible to inform adaptive therapies through feedback control. This allows for adjustment of therapeutic administration for a given patient based on phenotypic and metabolomic state. For example, the concentration of a specific drug could be controlled directly by measuring its concentration in circulation or the concentration of a specific drug could be controlled by measuring the concentration of related metabolites, or linked biomarkers.

Determining Pharmacokinetic Parameters

By facilitating real time monitoring of in vivo analyte concentrations, including plasma concentrations, the disclosed methods, devices and systems facilitate the determination of a variety pharmacokinetic parameters for pharmacologically active agents. For example, pharmacokinetic parameters such as peak plasma concentration ($C_{max}$), minimum plasma concentration ($C_{min}$), steady state concentration ($C_{ss}$), time to reach $C_{max}$ ($T_{max}$), plasma half-life ($T_{1/2}$), area under curve (AUC), volume of distribution (Vd), bioavailability and clearance may be readily determined using the methods, devices and systems of the present disclosure.

Aptamer Compositions

The present disclosure provides specific DNA aptamer compositions which find use in the disclosed methods, devices and systems.

A cocaine/procaine binding aptamer is provided, wherein the aptamer includes a DNA sequence having at least 90%, e.g., at least 95%, or 100%, sequence identity with the DNA sequence set forth in SEQ ID NO: 3.

A kanamycin-binding aptamer is provided, wherein the aptamer includes a DNA sequence having at least 90%, e.g., at least 95%, or 100%, sequence identity with the DNA sequence set forth in SEQ ID NO: 2.

A doxorubicin-binding aptamer is provided, wherein the aptamer includes a DNA sequence having at least 90% e.g., at least 95%, or 100%, sequence identity with the DNA sequence set forth in SEQ ID NO: 1.

In some embodiments, one or more of the above aptamers include a detectable label as described herein, e.g., a redox reporter, bound thereto.

In some embodiments, one or more of the above aptamers is immobilized on a solid support, e.g., in a microfluidic device channel and/or on an electrode according to the present disclosure.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., s or sec, second(s); min, minute(s); h or hr, hour(s); and the like.

Materials and Methods

The following materials and methods were utilized in connection with EXAMPLES 1-5 below.

Device Design and Fabrication:

The Microfluidic Electrochemical Detector for In vivo Continuous monitoring (MEDIC) device measures 58 mm×11 mm with a thickness of 2 mm, and is comprised of two layers of polydimethylsiloxane (PDMS) sandwiched between two glass wafers. The fabrication procedure is detailed below and illustrated in FIG. 2.

Two borofloat glass wafers (top and bottom), each 10 cm in diameter and 500 μm thick, were cleaned by sequential immersion in acetone, isopropanol and deionized water (DI). Gold working, counter and reference electrodes were then patterned onto the top wafer at 8-mm intervals photolithographically and electron-beam evaporated to a thickness of 200 nm on 20-nm titanium adhesion layers. Subsequently, a CNC mill with 1.1-mm diamond bit was used to drill fluidic vias (two inlets, one outlet) in the top wafer. The top and bottom wafers were then diced into device pieces with dimensions of 58 mm×11 mm and 53 mm×11 mm, respectively.

The 500-μm-wide top (buffer) and bottom (blood) flow channels were both cut from a 250-μm-thick PDMS sheet using a cutting plotter. The buffer channel was first bonded to the diced electrode glass substrate via 10-s corona-ozone treatment. The blood channel was bonded to the buffer channel, and then to the bottom glass substrate, each with the same ozone treatment. Alignment was performed under a standard inverted microscope via an x-y-z-θ stage and vacuum chuck. Fluidic port connectors were glued onto the device with 5-minute epoxy readying the chip for probe immobilization.

Probes, Preparation, and Immobilization

Aptamer probes were synthesized with the following sequences: DOX-probe: 5'-HS—$(CH_2)_6$-ACC ATC TGT GTA AGG GGT AAG GGG TGG T-MB-3' (SEQ ID NO: 1), Kanamycin-probe: 5'-HS—$(CH_2)_6$-GGG ACT TGG TTT AGG TAA TGA GTC CC-MB-3' (SEQ ID NO: 2). DOX-probe is a truncated form of an anthracycline aptamer. A region of the aptamer suspected of supporting a hairpin structure was selected, with an apparent active binding site in the base. The stem was engineered to enable effective signal transduction through stabilization of the folded state. The kanamycin probe was adapted from that described in Rowe et al. *Analytical chemistry* 82, 7090-5 (2010). Each probe was thiolated at the 5'-end to facilitate self-assembly on the gold working electrodes, and conjugated with an MB redox label at the 3'-end to enable target binding-induced charge transfer modulation. Prior to probe immobilization, the gold electrodes were first cleaned via cyclic voltammetry, with twelve potential sweeps ranging from −0.8 to 0.9 V (with respect to the platinum reference electrode) applied at 0.1 V·s$^{-1}$ with a sample interval of 0.001 V and 10 μA sensitivity in 50 mM $H_2SO_4$. Subsequently, the chamber was flushed with DI water, followed by the addition of probe solution. The probe solution was prepared by adding 2 μL of 10 mM tris(2-carboxyethyl)phosphine (TCEP) to 1 μL of 200 μM probe stock and incubating at room temperature for 60 minutes to enable cleavage of disulphide bonds. The solution was then diluted to 2 μM in 1× saline-sodium citrate (SSC) buffer for effective self-assembly. The chip was incubated with probe solution for 1 hour at room temperature, permitting the thiolated aptamer to form a monolayer on the gold electrode surface. The chamber was then flushed with 5 mL DI water for 5 minutes, and the remaining electrode area was incubated for two hours in passivation solution, consisting of 1 μL of stock 6-mercaptohexanol diluted to 3 mM in DI water. The chamber was flushed again with DI water and filled with 1×SSC, after which the device was stored at 4° C. until use.

Voltammetry

Electrochemical measurements were conducted with an electrochemical analyzer (730B, CH Instruments, Austin, TX). The chip was connected via 8-pin card-edge connector and subjected to SWV scans. Working electrodes were scanned in continuous succession with an average scan period of 8 seconds. To accommodate potential shifts due to the non-ideal on-chip pseudo-reference electrodes, a 400 mV potential range was scanned to reliably capture the MB redox peak. For optimal frequency determination for the KDM, frequency-sweep scans were performed from 5 Hz to 800 Hz, with amplitude of 25 mV. A custom peak-fitting script was created to fit the SWV measurements with a Gaussian curve on a hyperbolic baseline. Peak currents were then normalized to a baseline peak current to generate signal gain. Unless otherwise noted, all reported gains were obtained via KDM with the difference divided average of gains from 7.5 Hz and 75 Hz signals.

Fluidic Instrumentation

All flow to the device was controlled via syringe pump. The MEDIC input port was connected to an intravenous cannula for animal studies, or multiport valve for in vitro studies. The valve was used to select samples bearing different target concentrations. A 3 mL syringe loaded with 1×SSC was placed in a pump and connected to the buffer port on the MEDIC device via a 30-cm length of Tygon® tubing, with 2.29-mm outer diameter (OD) and 0.76-mm inner diameter (ID). The MEDIC device output port was connected to a primed but otherwise empty 10 mL "waste" syringe placed in a second pump, via ¹⁄₁₆-inch OD and 0.5-mm ID Teflon® tubing. To monitor flow rates in real time, a flow meter was employed in-line between the output port and syringe pump. The buffer layer was established by engaging the buffer pump at 0.25 mL·h$^{-1}$. Simultaneously, sample was continuously drawn into the device by engaging the waste pump at 1 mL·h$^{-1}$.

Human Whole Blood

Male human whole blood was obtained with sodium citrate anticoagulant within approximately one week of the date drawn from the donor. Whole blood was refrigerated at 4° C. until use. Prior to use, blood was warmed to room temperature and then passed through a 40 μm pore cell-strainer to remove or break up any large aggregates while letting blood constituents pass through. Target drug was then added to the blood to achieve the desired dose. To minimize dilution, corresponding 100× stock solutions of drug in 1×SSC were used. Whole blood was otherwise unmodified.

Probe Characterization

Probes were characterized in terms of affinity, specificity and kinetic response. For affinity measurements, a dose-response curve was obtained by subjecting the probe to DOX concentrations (for the DOX-probe) ranging from 50 nM to 10 μM in 1×SSC at a flow-rate of 1 mL·h$^{-1}$. At each concentration, the signal was permitted to equilibrate and then ten subsequent readings were obtained from two separate electrodes and averaged as the reported values. The same procedure was applied for specificity characterization, where DOX was injected at 1 μM while off-target reagents mitomycin-C (MTC), ifosfamide (Ifex), Mesna, dacarbazine (DTIC) or cisplatin (CDDP) were injected at 1 mM. Kinetic measurements were performed in a reaction-limited regime by flowing target-free buffer at 10 mL·h$^{-1}$ for 5 minutes to obtain a stable baseline, followed by a 5-minute 1 μM DOX pulse, and then back to buffer. Voltammograms were taken in immediate succession to provide maximal temporal resolution. Dose-response curves were obtained by fitting data to a one-site binding model, and kinetic-response curves were obtained by fitting data to a one-phase association and dissociation model.

LOD was calculated as the concentration that gives a signal three baseline standard deviations ($s_{baseline}$) above zero, $$LOD = K_D \frac{3s_{baseline}/D_{max}}{1 - 3s_{baseline}/D_{max}}.$$

To determine the dynamic range, the maximum detectable concentration (MDC) was calculated as the concentration where the average is three standard deviations less than maximum signal. Here $s_{max}$ is the average standard deviation of the four largest concentrations used, $$MDC = K_D \frac{(D_{max} - 3s_{max})/D_{max}}{1 - (D_{max} - 3s_{max})/D_{max}}.$$

Continuous Diffusion Filter (CDF) Characterization

COMSOL Multiphysics V4.2a (COMSOL Inc., Los Angeles, CA) was used to simulate target and non-target diffusion in the microchannel in three dimensions via laminar flow and transport of diluted species modules. To simplify the simulation geometry, the straight portion of the channel from the junction of the two vertically-stacked flows to the outlet region was focused on. Based on an expected operational sample-to-buffer throughput ratio of 3:1, the domain depths were assigned to 375 µm and 125 µm, respectively. Input flow-rates were defined at 0.75 and 0.25 mL·h$^{-1}$ for buffer and sample respectively, with open pressure defined at the output. Buffer was represented as water, while the blood sample was approximated as water with density increased to 1060 kg·m$^{-3}$ and viscosity increased to 4 mPa·s. A diffusion constant of 1×10$^{-9}$ m$^2$·s$^{-1}$ was assumed for DOX. As blood protein interferents associated with biofouling, HSA, IgG and fibrinogen were assigned estimated diffusivities of 5, 4 and 2×10$^{-11}$ m$^2$·s$^{-1}$, respectively. Analytes were supplied in the sample stream at a concentration of 1 µM at the sample input and convected according to the prior-solved velocity field, and reported concentrations were normalized by this value for the respective species. Solving for the velocity field and then the convection diffusion equation yields the concentration field throughout the channel. An x-y cross-section was taken at the top of the channel in the plane of the electrodes (FIG. 3, Panel A), scaled at 20% in x with respect to y. This cross-section confirms an expected transport fraction in excess of ~50% of input at a point 20 mm from the junction, with parabolic isolines. Examination of y-z sections along the channel (FIG. 3, Panel B) showed diffusion of DOX from the target-rich flow stream to the initially pure buffer stream.

All confocal imagery data was obtained via Fluoview 1000 MPE (Olympus Corporation, Tokyo, Japan) with a 10× objective. To obtain unobstructed views of the channel, devices were fabricated exclusively for imaging that were identical to normal devices save the absence of electrodes. These were mounted upside-down on a microscope slide clipped to the microscope stage in order to prevent the connectors from occluding the view of the channel. With the device mounted upside down, the buffer and blood inputs were switched to enable normal operation with blood on the bottom and buffer on the top. The motorized stage enabled digital encoding of location data. The x-y origin was set at the center of the channel junction for a given device. All location data were thus derived from the stage readout with respect to junction center. All image depth data were likewise derived from the readout of the motorized nosepiece actuating in the z-axis. To image the buffer and blood streams, fluorescein and rhodamine WT fluorescent dyes were respectively added to each at 1:10,000 dilution from stock. The rhodamine and fluorescein dyes were excited with 559-nm and 473-nm lasers, respectively. To negate channel cross-talk, all images were collected via sequential illumination. To demonstrate flow stacking in the absence of diffusion, the flow-rates of the buffer and blood streams were increased 10-fold to 2.5 and 7.5 mL·h$^{-1}$, respectively, since small-molecule dye diffusion was readily observed under normal operating conditions.

KDM Characterization

The rate of charge transfer from the redox-labeled probe described herein is a function of the applied voltage, probe flexibility, and redox reporter location. At a fixed voltage, $$I = -F\frac{d[MB]}{dt} = F(k_1[MB] - k_{-1}[-leucoMB]),$$

where F is Faraday's constant, [MB] is the concentration of methylene blue, [leucoMB] is the concentration of reduced leucomethylene blue, and $k_1$ and $k_{-1}$ are the forward and reverse reaction rates, respectively. In the unbound probe conformation, the kinetics are slow and MB is gradually reduced to leucoMB. However, in the bound confirmation, the kinetics are fast and MB is reduced rapidly. The probe was interrogated at multiple SWV frequencies, by varying the pulse-width $$\left(\frac{1}{2f}\right)$$

Figure 6:
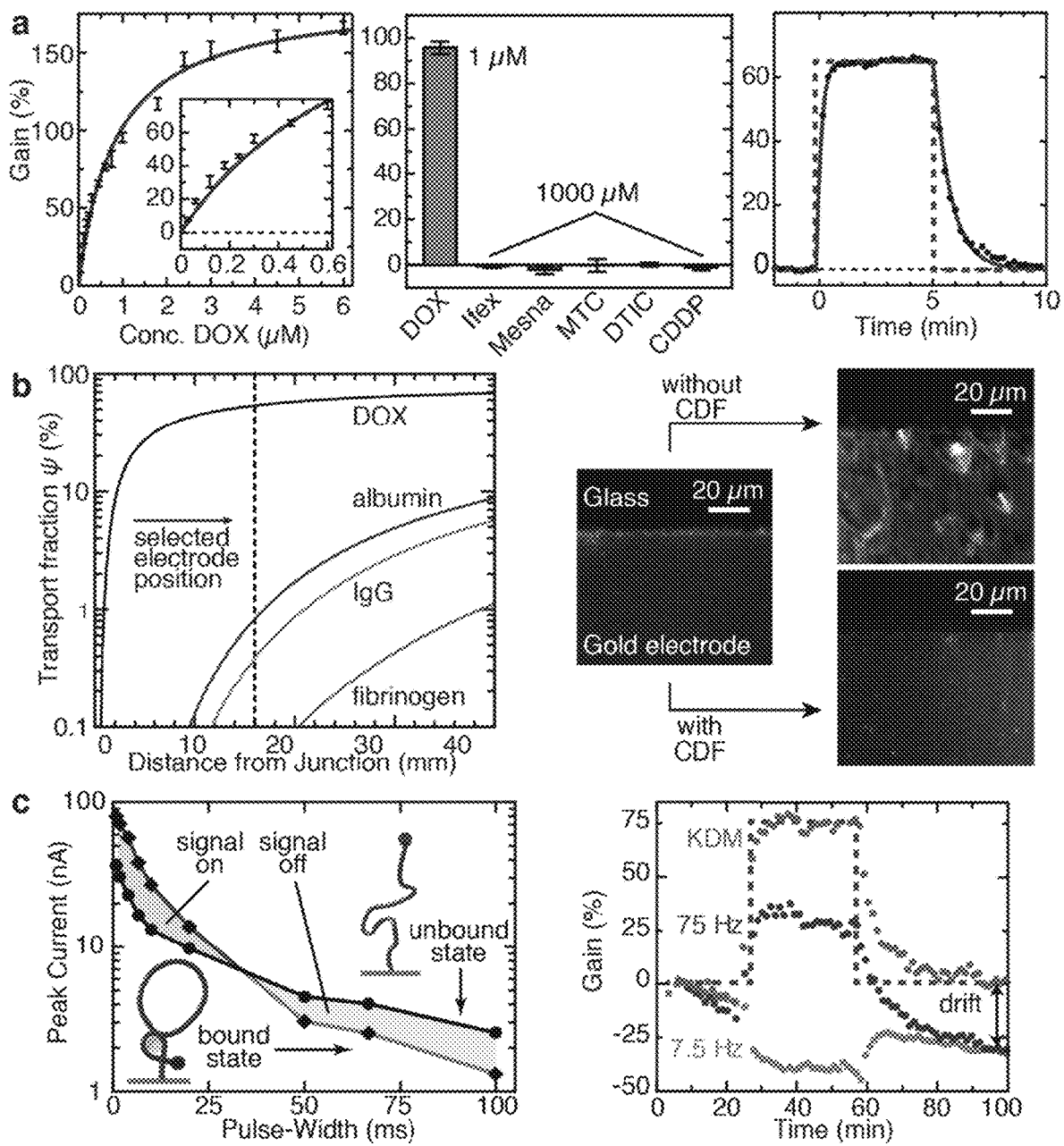
FIG. 6 illustrates the basic aspects of a MEDIC system according to an embodiment of the present disclosure. (a) Characterization of the DOX probe. (Left) Dose-response of the sensor showing a LOD of 10 nM and dynamic range of 0.1-10 µM. Error bars were obtained from 20 measurements. (Middle) The probe is specific to DOX and does not respond to far higher concentrations of other drugs. Error bars were obtained from 15 measurements. (Right) The sensor responds rapidly to its target ($k_{on}$=3.0±0.35 µM$^{-1}$·min$^{-1}$ and $k_{off}$=1.35±0.05 min$^{-1}$). (b) CDF design and performance. (Left) Simulations demonstrate that DOX efficiently crosses the CDF ($\psi_{DOX}$=54%) while interferents are rejected ($\psi_{interferents}$<1%). (Right) Optical micrographs show that the CDF protects the sensor surface from fouling. (c) Mechanism and effectiveness of KDM. (Left) In the unbound state, MB is slowly reduced, yielding a gradual decay in current, whereas MB is rapidly reduced in the target-bound state. Thus the response can be inverted from "signal-on" to "signal-off" by changing the interrogation frequency. (Right) Without KDM, the response to a DOX pulse (dashed line) at 75 or 7.5 Hz exhibits significant drift. KDM minimizes drift and increases signal amplitude.

(FIG. 4), to observe the rate of MB reduction. At short pulse-widths, higher current in the bound (FIG. 6, Panel C, Left, red) was observed compared to the unbound state (FIG. 6, Panel C, Left, black), as the faster kinetics allow more rapid reduction of MB. However this rapid reduction results in depletion of MB, such that with longer pulse-widths, lower current in the bound state was observed (FIG. 6, Panel C, Left, blue).

The KDM signal (d) is obtained by taking the difference of the signal-on ($G_{on}$) and signal-off ($G_{off}$) and dividing by the average as $$D = \frac{G_{on} - G_{off}}{(G_{on} + G_{off})/2}.$$

SNR was defined as $$SNR = \frac{D_{target}}{\sqrt{s_{baseline}^2 + s_{target}^2}},$$

where $\overline{D_{target}}$ is the average signal in the presence of target and $s_{target}$ is the standard deviation.

Quantification In Vitro

Concentration (c) vs. differential gain (d) curves were fit to a two-parameter ($K_D$ and $D_{max}$) isothermal single binding-site model, $$D = D_{max} \frac{C/K_D}{1 + C/K_D}.$$

To demonstrate the capacity to perform MEDIC sensing with a handheld unit instead of a benchtop electrochemical analyzer, the PalmSens EmStat[2] (Palm Instruments BV, Houten, Netherlands) was utilized. A comparable effective signal was observed; to account for instrument differences, KDM was performed with constituent frequencies of 150 and 5 Hz, and a separate dose-response curve was obtained.

Live Animal Studies

Figure 5:
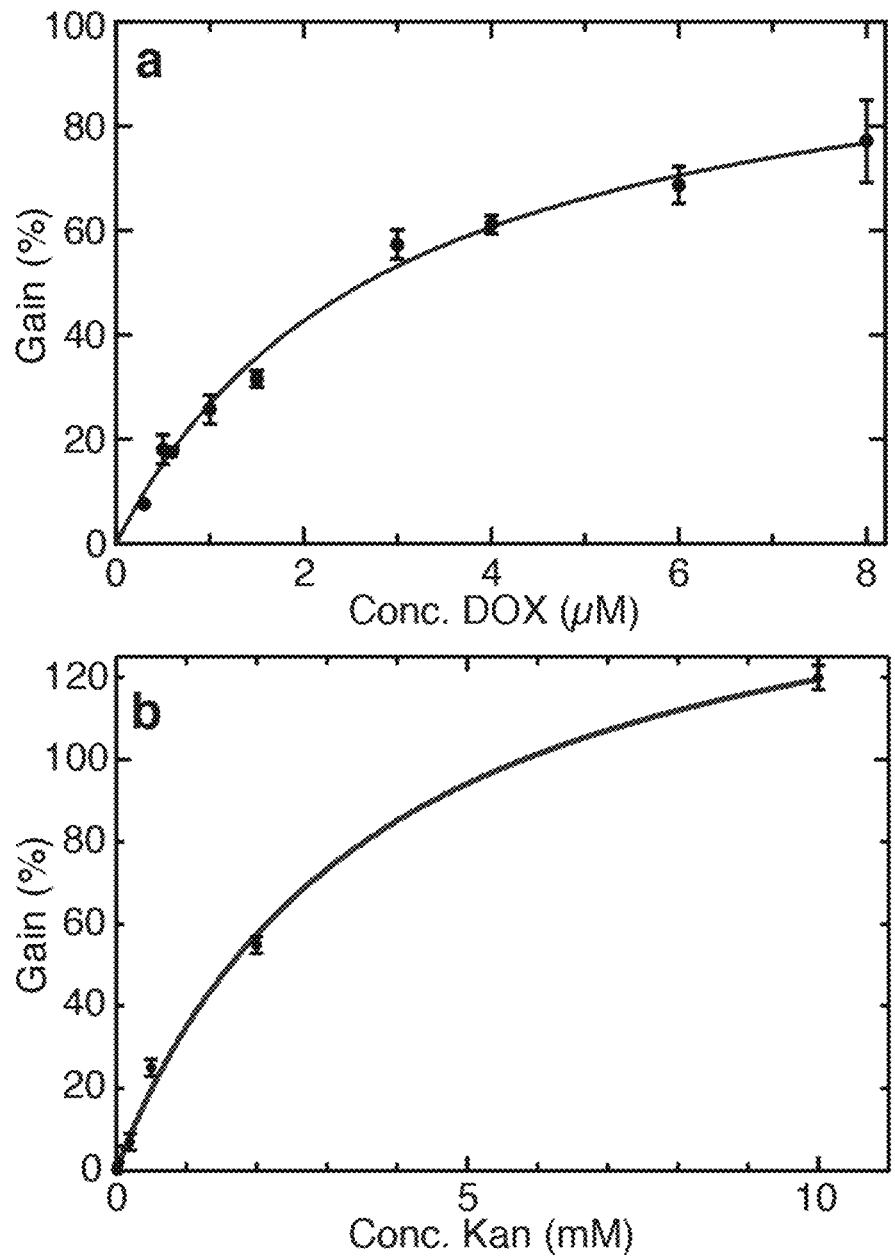
FIG. 5 shows dose response curves obtained in whole blood in vitro when an embodiment of the MEDIC system was targeted to detect either DOX (a) or kanamycin (b).

All rats used in this work were Sprague-Dawley males from Charles River Laboratories (Hollister, CA, USA). To safely mount the device and catheters, rats were sedated throughout the duration of the experiment via isoflurane gas (1-4%) and ketamine/xylazine (56.25 mg·kg$^{-1}$ and 7.5 mg·kg$^{-1}$ respectively). Animals were placed dorsal side down on a heating pad. The right jugular vein was isolated and catheterized to provide an intravenous injection port. An initial injection of 0.41 mL heparin solution (1000 U·mL$^{-1}$ USP) was performed, followed by periodic injections of 0.1 mL every 40 minutes to prevent clot formation in the catheters. The left jugular vein was isolated and cannulated. A 0.3 mL pre-drug injection control blood sample was taken and set aside for the duration of the experiment. The end of a 10-cm length of Tygon® tubing (2.29-mm OD and 0.76-mm ID) was inserted into the cannula to connect the intravenous blood source to the blood port of the MEDIC device. The remaining fluidic instrumentation was configured as described in the prior section. Target concentrations were adjusted for a constant 0.3 mL injection volume, and injected via the input catheter in a 30-second bolus at >30 min intervals. Upon completion of each experiment, subjects were euthanized via intravenous Euthasol® injection. The MEDIC input tube was then redirected to the control blood to obtain post-experiment readings of zero-target blood samples. Observed concentrations were derived from a dose-response calibration curve obtained a priori (FIG. 5). Animal body surface area was calculated as per the correlation described by Lee, M. O. *American Journal of Physiology—Legacy Content* 89, 24-33 (1929), and all dosing was normalized to this estimated quantity.

The following materials and methods were utilized in connection with EXAMPLES 6-8 below.

Device Design and Fabrication:

A MEDIC device was designed and fabricated as described above for Examples 1-4.

Probes, Preparation, and Immobilization

A cocaine/procaine binding aptamer was synthesized with the following sequence: 5'-HS—(CH$_2$)$_{11}$-AGA CAA GGA AAA TCC TTC AAT GAA GTG GGT CG-(CH$_2$)$_7$-MB-3' (SEQ ID NO: 3). The probe was thiolated on the 5'-end to facilitate self-assembly on the gold working electrodes, and conjugated with a methylene blue redox label at the 3'-end to enable target binding-induced charge transfer modulation. To immobilize the probe on the gold surfaces, the electrodes were first cleaned via cyclic voltammetry, with twelve potential sweeps ranging from –0.8 to 0.9 V (with respect to the platinum reference electrode) applied at 0.1 V s$^{-1}$ with a sample interval of 0.001 V and 10 μA sensitivity in 50 mM H$_2$SO$_4$. Subsequently, the chamber was flushed with deionized (DI) water, followed by the addition of probe solution. Probe solution was prepared by adding 2 μL of 10 mM tris(2-carboxyethyl)phosphine (TCEP) to 1 μL of 200 μM probe stock and incubating at room temperature (RT) for 60 minutes to enable cleavage of disulphide bonds, after which it is diluted to 2 μM in 1×SSC (saline-sodium citrate) buffer for effective subsequent self-assembly. The chip was incubated for 1 hour at room temperature, permitting the thiolated aptamer to form a self-assembled monolayer on the gold electrode surface. The chamber was then flushed with 5 mL of DI water over 5 minutes, and the remaining electrode area was incubated for two hours in passivation solution, consisting of 1 μL of stock 6-mercaptohexanol diluted to 3 mM in DI. The chamber was flushed again with DI water and filled with 1×SSC, after which the device was stored at 4° C. until use.

Voltammetry

Electrochemical measurements were conducted with an electrochemical analyzer (730B, CH Instruments, Inc., Austin, TX). The chip was connected via a 8-pin card-edge connector and subjected square wave voltammetry scans. The six working electrodes were scanned in continuous succession with scan period of 1 minute for a given electrode. The interrogation potential ranged from –0.7 V and –0.2 V at a frequency of 60 Hz, with increment of 1 mV and amplitude of 25 mV at current sensitivity of 200 nA. SWV curves were aligned by peak potential to correct for drift due to the on-chip platinum pseudo-reference electrodes.

Fluidic Instrumentation

Flow to the device was controlled via syringe pump with samples loaded into 5 mL polystyrene syringes. Syringes were connected to the device via 360 μm outer diameter (OD), 150 μm inner diameter (ID) PEEK capillary tubing with luer lock and chip surface connectors. Input samples bearing different target concentrations were selected via a multiport valve. The output was directed to a waste collection tube via 1/16 inch OD and 0.5 mm ID Teflon® tube.

Whole Blood

Male human whole blood with sodium citrate anticoagulant was obtained within approximately one week of the date drawn from the donor. Whole blood was refrigerated at 4° C. until use, at which time it was warmed to room temperature. Prior to use, blood was passed through a 40 μm pore cell-strainer to remove or break-up any large aggregates while letting usual blood constituents pass through. Prior to use, procaine hydrochloride was added to whole blood to achieve the desired dose. To minimize the dilution of the whole blood, corresponding 100× procaine stock solutions in 1×SSC buffer were used. Whole blood was otherwise unmodified.

Finite Element Simulation Details

COMSOL Multiphysics V4.0 was used to simulate cocaine diffusion in the microchannel in three dimensions via laminar flow and transport of diluted species modules. Transport of cocaine was simulated, but experimental validation was performed using procaine. It should be noted that the cocaine/procaine binding aptamer binds cocaine and procaine with similar affinity. In addition, as cocaine and procaine possess similar molecular mass they exhibit similar transport through the CDF. To simplify the simulation geometry, only the straight portion of the channel was included, from the junction of the two vertically-stacked flows to the outlet region. Based on an expected operational sample to buffer throughput ratio of 4:1, the domain depths were assigned to 400 μm and 100 μm, respectively. Average input flow velocities in the direction of the channel were applied at the input boundary at 1 mm·s$^{-1}$. Open pressure was defined at the output. Water was used to represent that buffer solution and water with viscosity increased to 4 mPa·s and density increased to 1060 kg·m$^{-3}$ is used to approximate the otherwise non-Newtonian blood. Cocaine analyte, assigned a diffusion constant of 3×10$^{-10}$ m$^2$·s$^{-1}$, was supplied at a concentration of 1 mM at the sample input and convected according to the prior-solved velocity field.

Confocal Microscopy

Confocal imagery data was obtained via the Olympus Fluoview 1000 MPE under a 10× objective. To obtain unobstructed views of the channel, electrode-free devices were made exclusively for imaging which were fabricated identically to the normal devices save the absence of electrodes. Further, these devices were mounted upside-down on a microscope slide clipped to the microscope stage in order to prevent the connectors from occluding the view of the channel as well. With the device mounted upside down, the buffer and blood inputs were thus switched to enable normal operation with blood on the bottom, and buffer on the top. The motorized stage enabled digital encoding of location data. The x-y origin was set at the center of the channel junction for a given device. Location data is thus derived from the stage readout with respect to junction center. Image depth data is likewise derived from the readout of the motorized nosepiece actuating in the z-axis. To image buffer and blood streams, fluorescein and rhodamine WT flourescent dyes were added to each respectively at 1:1000 dilution from stock. The rhodamine and fluorescein dyes were exited with a 559 nm 473 nm lasers respectively. To negate channel cross-talk, all images were collected via sequential illumination.

Example 1

Microfluidic Electrochemical Detector for In Vivo Continuous Monitoring (Medic)—Probe Validation As a proof-of-concept, MEDIC, depicted generally in FIG. 1, was used to measure the in vivo concentration of doxorubicin (DOX), a widely used chemotherapeutic, in live rats. DOX was chosen because its pharmacokinetics vary substantially across the population and change over the course of treatment.

The DOX probe was designed based on a previously-described DNA aptamer, selected in vitro to bind the anthracycline drug. The 3' end was covalently conjugated to methylene blue (MB), which serves as an electrochemical reporter. Its 5' end was thiolated for self-assembly onto the gold working electrodes of the electrochemical sensor. Target binding induces a conformational change in the aptamer that modulates electron transfer rate between MB and the electrode. The resulting change was measured using square-wave voltammetry (SWV) and signal gain was defined as the relative change in current at the MB reduction peak, which is a direct function of DOX concentration in solution.

The DOX probe responded sensitively and rapidly to its specific molecular target. Probe sensitivity was measured by fitting signal gain to a Langmuir isotherm and obtaining its apparent $K_d$ (824 nM±18 nM) (FIG. 6, Panel A, Left). The sensor achieved a limit of detection (LOD) in buffer of 10 nM, and a dynamic range spanning the entire 0.1-10 μM therapeutic range for the drug. Importantly, the sensor did not respond to 1,000× greater concentrations of ifosfamide (Ifex), mesna, mitomycin-C (MTC), dacarbazine (DTIC) or cisplatin (CDDP), chemotherapy agents commonly administered with DOX (FIG. 6, Panel A, Middle). In addition, the sensor rapidly responds to its target; after a 5 minute pulse of 600 nM DOX, $k_{on}$=3.0±0.35 μM$^{-1}$·min$^{-1}$ and $k_{off}$=1.35±0.05 min$^{-1}$ were measured. This allows the probe to reach 90% saturation within 45 s and then return to 10% of baseline within 100 s (FIG. 6, Panel A, Right). Since the alpha-phase plasma clearance time of DOX in humans is 6-26 min, the temporal resolution of the sensor is sufficient for clinical applications.

Example 2

Medic—Continuous Flow Diffusion Filter (CDF)

Although aptamer-based electrochemical sensors have been demonstrated in serum, applications in whole blood have been thwarted by fouling. To address this, a continuous-flow diffusion filter (CDF) was established by vertically stacking laminar flow streams of blood and an isotonic buffer within the chip (FIG. 1, Panel C, and FIG. 2). Because of its high diffusivity, DOX rapidly diffuses across the CDF while larger, lower-diffusivity interferents generally do not reach the sensor during their transit through the device. Unlike many physical filters, the liquid-phase CDF does not saturate, and protects the probe against nuclease degradation and enables optimization of buffer conditions to achieve maximum performance.

Figure 7:
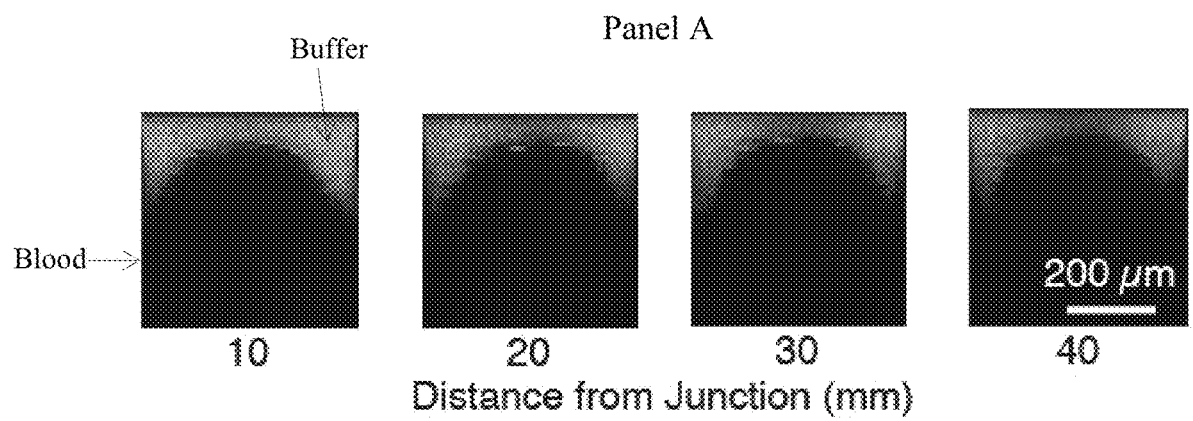
FIG. 7 shows the results of characterizing a continuous diffusion filter (CDF) according to an embodiment of the present disclosure. Panel A—Confocal microscopy shows that the buffer (blue) and blood (black with red boundary) streams remain separate throughout the device. Panel B—Visualizing the thickness and shape of the CDF in buffer under different flow conditions. Top row: Dual buffer flow at 1:4 throughput, confirming maintenance of the diffusion layer throughout the MEDIC device channel. Middle row: Buffer and whole blood at a 1:1 flow ratio yield a curved flow pattern due to mismatched viscosity. Bottom row: Buffer and whole blood at a 1:4 throughput ratio results in an intact, though non-uniform, diffusion barrier.
Figure 7:
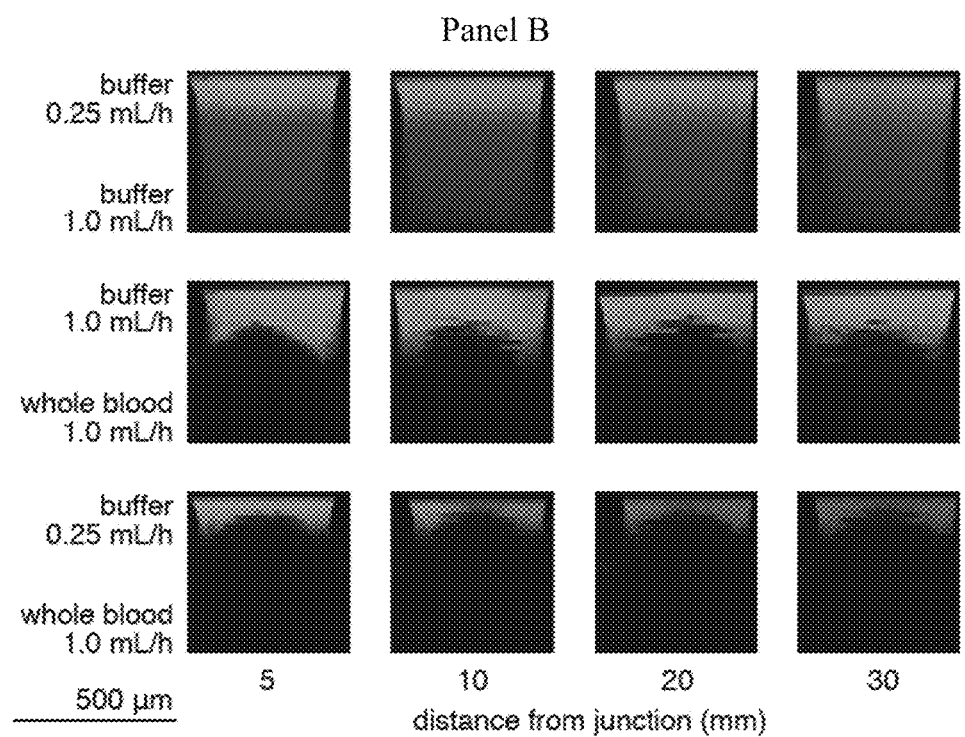

The CDF was designed by numerically modeling the transport of DOX and typical blood-borne interferents, human serum albumin (HSA), immunoglobulin G (IgG) and fibrinogen. A finite element model of the MEDIC channel was created to solve for velocity and concentration distributions. CDF thickness and analyte residence time are adjustable by controlling the total flow and the ratio of the two flow-rates. A 125-μm-thick CDF and total flow-rate of 1 mL·h$^{-1}$ yielded a Reynolds number ~0.1, enabling laminar flow stacking throughout the device. This was verified by loading buffer and blood with fluorescent dyes and imaging via confocal microscopy (FIG. 7, Panel A), which produced consistent results across multiple flow-rate ratios (FIG. 7, Panel B).

Figure 3:
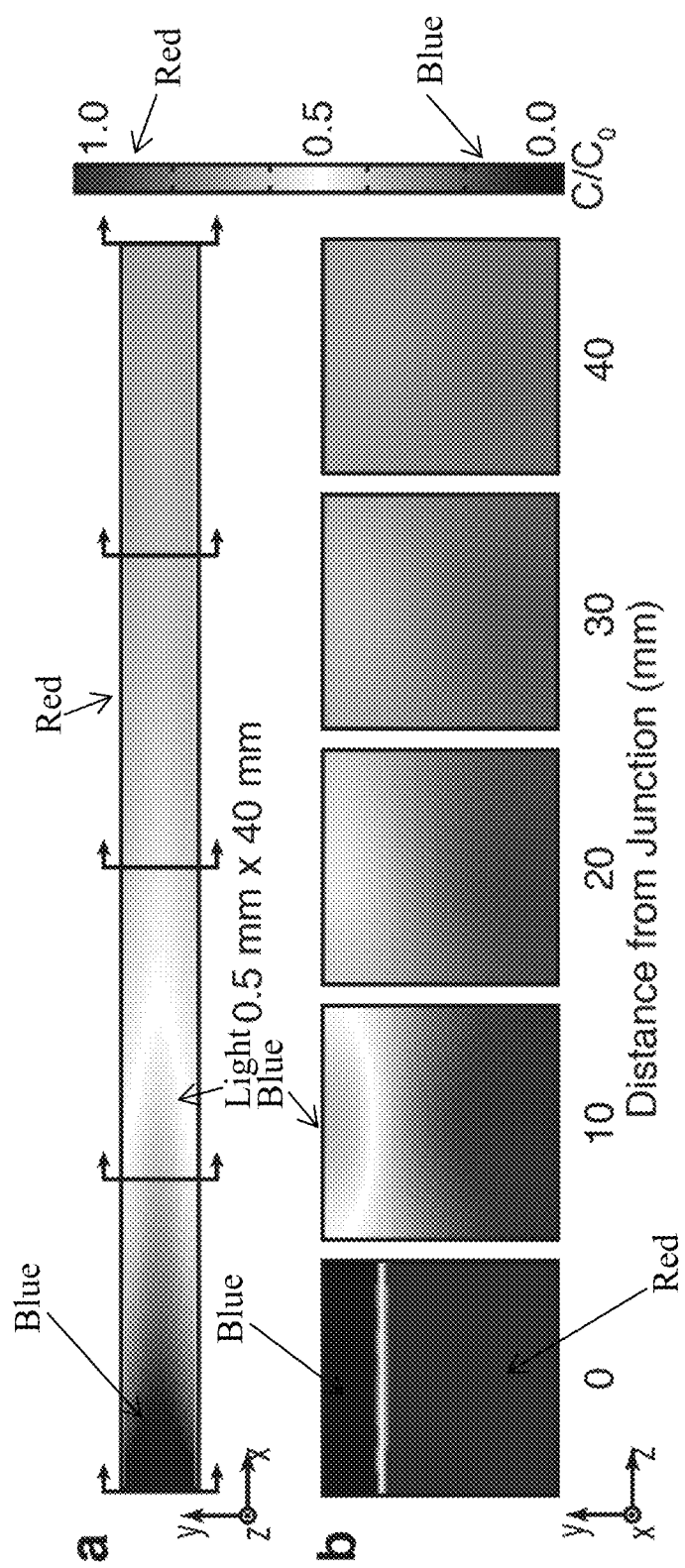
FIG. 3 shows a finite element model of diffusive transport of target in the MEDIC channel according to an embodiment of the present disclosure. The normalized target concentration ($C/C_0$) field illustrated in (a) the longitudinal cross-section of the sensing surface of the channel, and (b) at transverse cross-sections of the channel at increasing distances from the fluidic junction. Note that target is readily transported from the bulk sample (initially red) through the buffer stream (initially blue) given increased residence time in the channel.

Average concentrations of DOX and interferents were calculated at the sensor surface ($C_{surf}$) as a function of position along the channel and normalized to their input concentration ($C_0$) to yield the transport fraction, $\psi=C_{surf}·C_0^{-1}$ (FIG. 3). The CDF was configured to yield a transport fraction that is high for DOX and low for interferents (FIG. 6B, Left). Sensor placement proved optimal 16 mm from the buffer/blood junction, where the CDF enables relative DOX enrichment ($\psi_{DOX}·\psi_{interferent}^{-1}$) of >65-fold over HSA, >140-fold over IgG and >1,000-fold over fibrinogen. Owing to their substantially lower diffusivities, blood cells are excluded even more efficiently. Imaging of the electrode surface before and after 20 min in flowing whole blood confirmed the effectiveness of the CDF in preventing fouling (FIG. 6B, Right).

Example 3

Medic—Kinetic Differential Measurement Technique (KDM)

To achieve accurate, long-term measurements, it is important to maintain high SNR and minimize drift. Differential measurement is a powerful technique to achieve this requirement, wherein a reference probe is utilized to obtain a common background signal that can be subtracted from the sensor's signal. Such measurements typically require a physically separate reference probe that is unresponsive to the target but otherwise yields an identical response to a variable backgroundforth. To overcome this limitation, a kinetic differential measurement technique (KDM), which requires only a single probe to auto-correct for variable background, enhances SNR, and enables absolute quantification of target concentration was developed.

Figure 4:
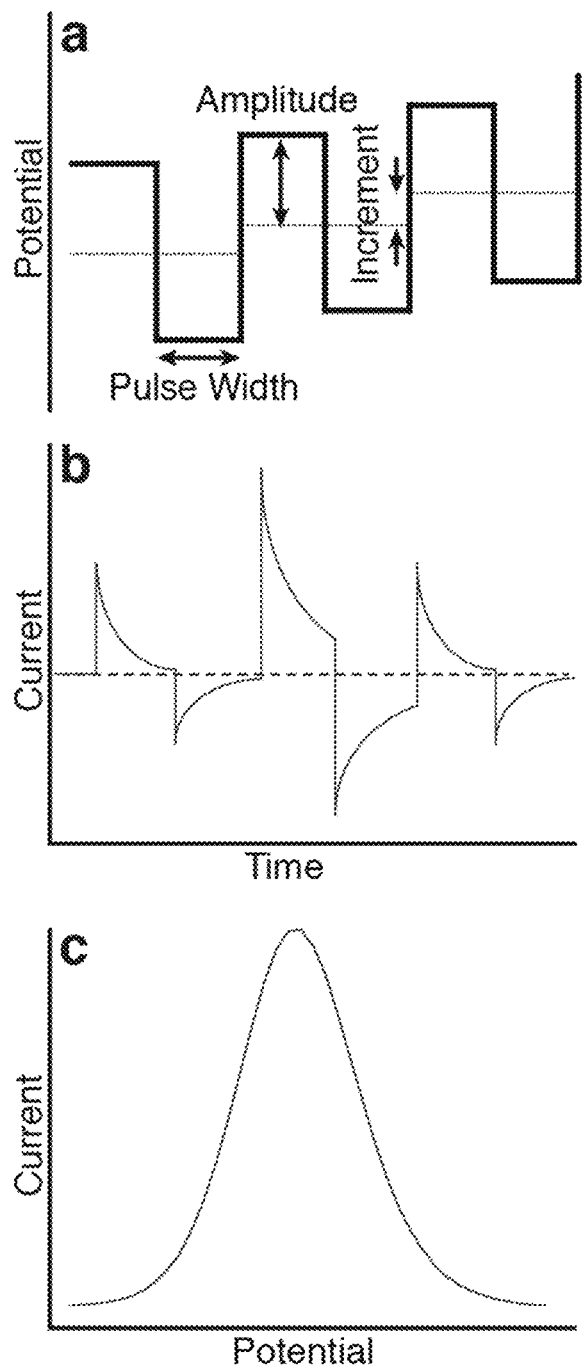
FIG. 4 shows a schematic illustration of square wave voltammetry (SWV). (a) Square-wave potential pulses of given amplitude and frequency are applied on a potential staircase at a given increment. (b) Redox current is generated from applied potential, with spikes decaying to steady state as the finite quantity of redox label approaches equilibrium at the given potential. (c) Voltammograms obtained from SWV by subtracting the forward and reverse currents at the end of each pulse for a given cycle.
Figure 8:
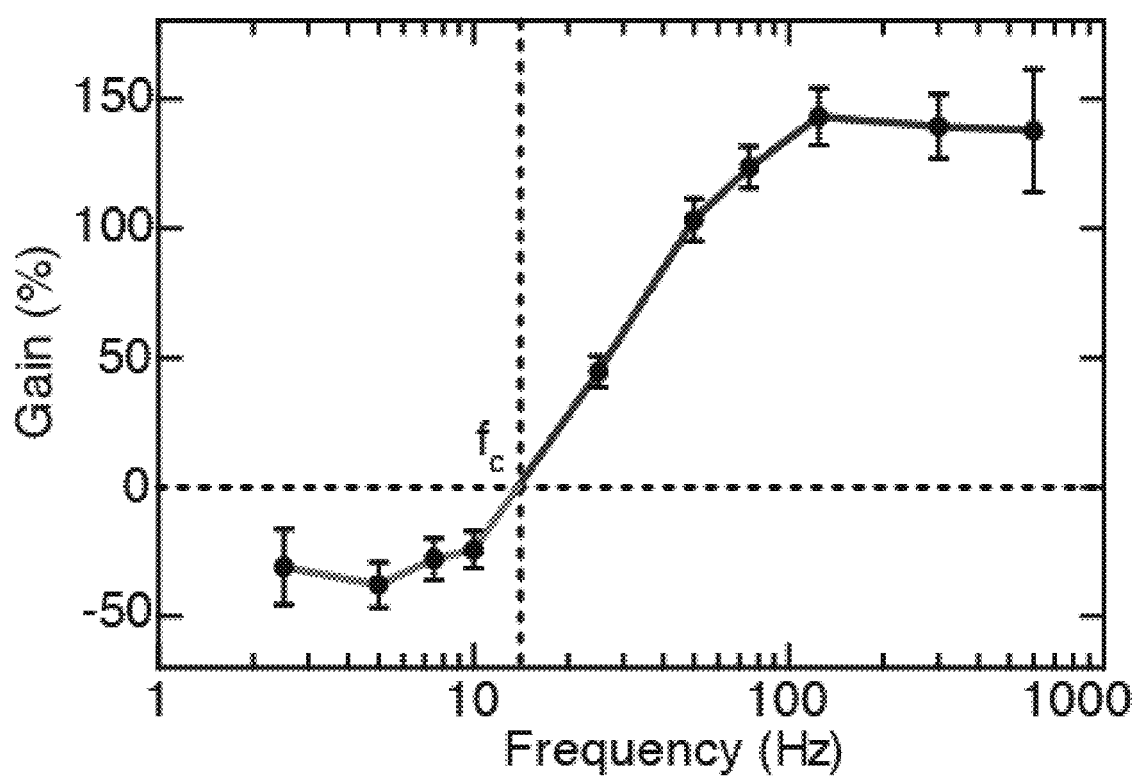
FIG. 8 shows a graph illustrating a "signal on" response above $f_c$ and "signal-off" response below $f_c$ for one embodiment of a conformation switching probe according to the present disclosure.
Figure 9:
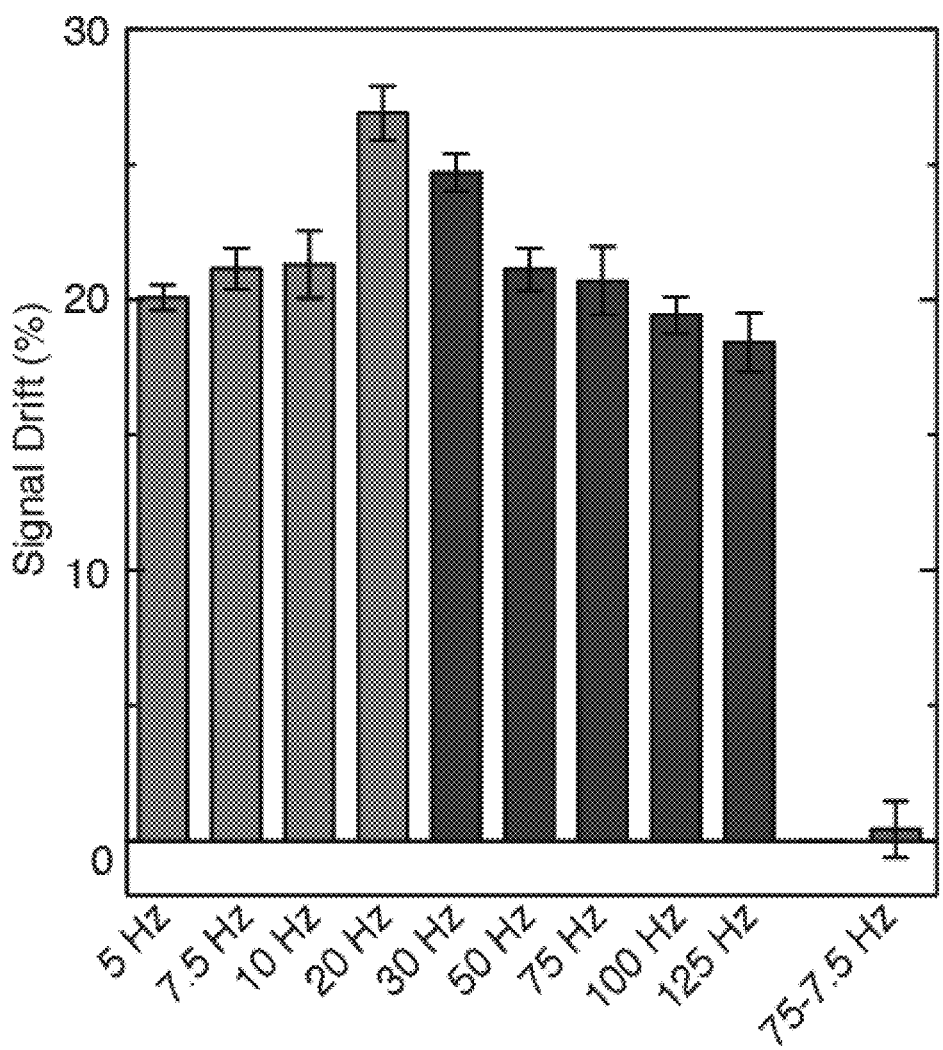
FIG. 9 provides a graph illustrating the frequency response of drift for an embodiment of a MEDIC system according to the present disclosure. Frequency-dependent signal drift is obtained at frequencies above and below $f_c$. By selecting frequencies with matching drift levels, the drift obtained from their differential is dramatically reduced. 7.5 Hz and 75 Hz proved to be well-matched frequencies that enabled minimization of signal drift.
Figure 10:
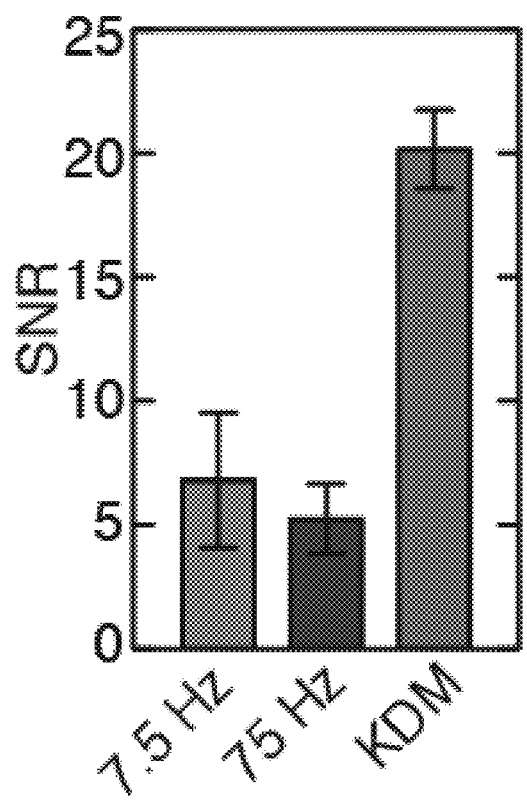
FIG. 10 provides a graph illustrating that kinetic differential measurement (KDM), as utilized in an embodiment of a MEDIC system according to the present disclosure, improves signal to noise ratio (SNR) by a factor of ~3. Means and standard deviations were obtained via triplicate measurements with independent chips.

KDM exploits the difference in charge transfer kinetics between the target-bound and unbound states of the probe. This difference occurs because the unbound probe adopts an unfolded conformation such that the MB reporter approaches the electrode surface infrequently, resulting in relatively slow electron transfer (FIG. 6, Panel C, Left). In contrast, the folded conformation of the target-bound probe constrains MB closer to the electrode, increasing the electron transfer rate. This difference allows one to obtain a "signal-on" response when interrogating using high frequency SWV and a "signal-off" at lower frequencies, with a crossover frequency ($f_c$) of ~11 Hz (FIGS. 4 and 8). Importantly, because these two output signals exhibit matching response to the background (FIG. 9), they can be differentially combined to eliminate drift. For example, while ~30% baseline drift was observed using frequencies of 75 and 7.5 Hz in response to a 2 µM pulse of DOX in whole blood over 90 min (FIG. 6, Panel C, Right), KDM reduced the drift to <2%. Moreover, because the two output signals differ in polarity, taking their difference enhances the SNR. For example, the signals at 7.5 and 75 Hz yielded SNRs of 6.8±2.7 and 5.2±1.5 respectively, which KDM improved to 20±1.6 (FIG. 10).

Figure 11:
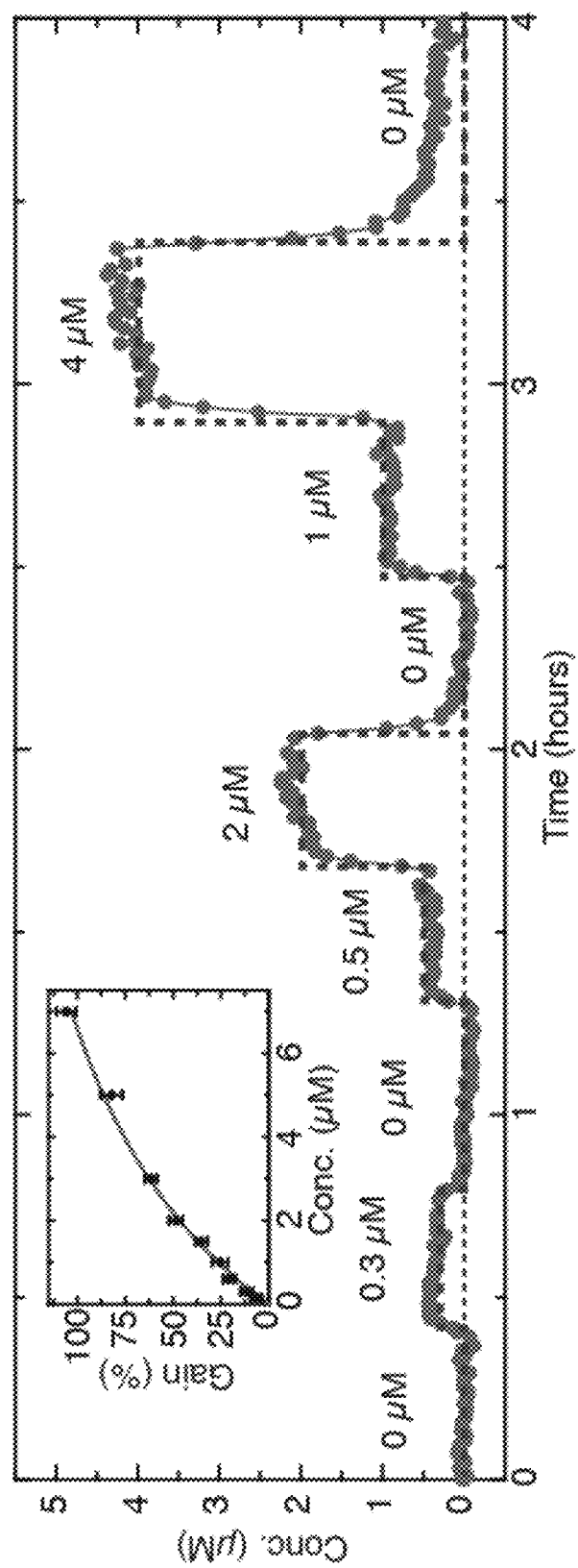
FIG. 11 provides a graph showing the continuous and quantitative in vitro measurement of DOX in whole blood (dotted line) relative to actual concentrations (large dashed line) using a MEDIC system according to an embodiment of the present disclosure. The inset provides a standard curve relating KDM signal to DOX concentration.

MEDIC can determine absolute analyte concentrations from KDM output (FIG. 11). To do so, a standard curve was constructed assuming a Langmuir isotherm (FIG. 11, Inset). After pulsing DOX at 0.3, 0.5, 1, 2 and 4 µM in whole blood (FIG. 11), MEDIC tracked concentrations with a highly stable baseline for 4 hours with an average error of 0.06 µM, verifying its ability to quantify unknown DOX concentrations in real-time.

Example 4

Continuous Real-Time Measurement Using Medic

Figure 12:
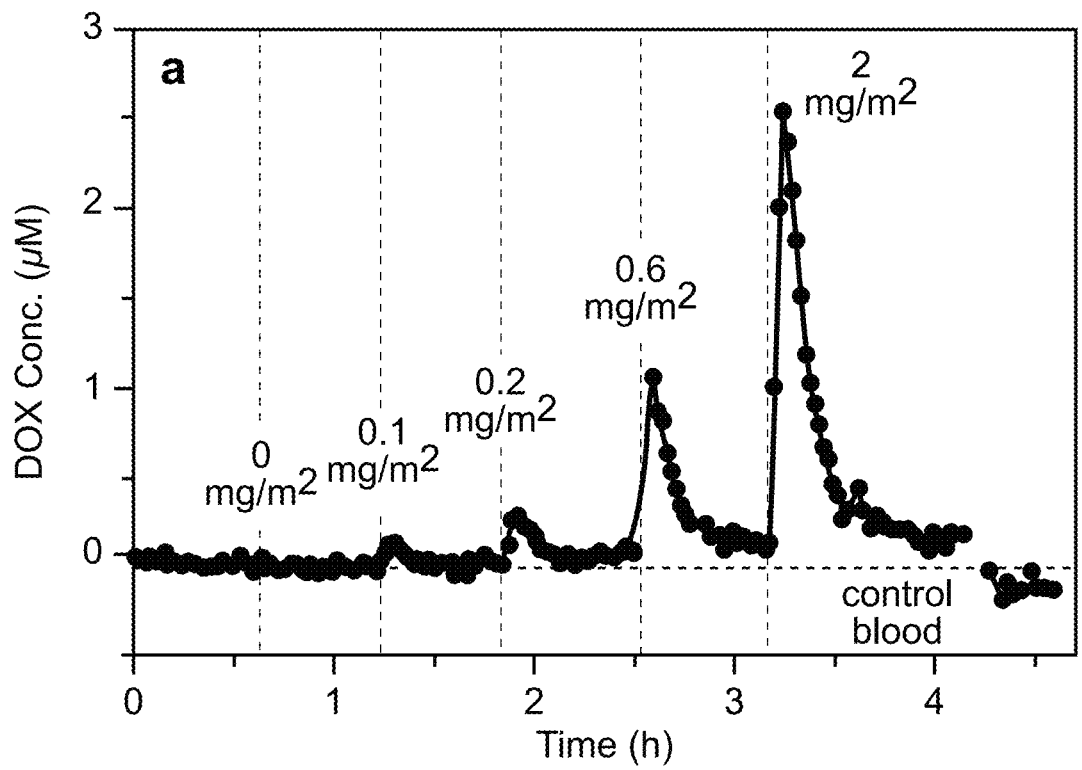
FIG. 12 provides graphs showing the real-time measurement of specific molecular analytes in blood of living rats using a MEDIC system according to an embodiment of the present disclosure. (a) MEDIC reliably measured changing in vivo concentrations with minimal signal drift over several hours. (b) Consistent peak concentrations and alpha-phase half-lives are obtained after two injections. (c) MEDIC revealed significant variability in alpha-phase half-life as a function of body surface area: across nine rats, a Pearson correlation coefficient of −0.73 was observed. (d) by exchanging the aptamer probe, continuous real-time measurement of in vivo kanamycin concentrations was achieved.
Figure 12:
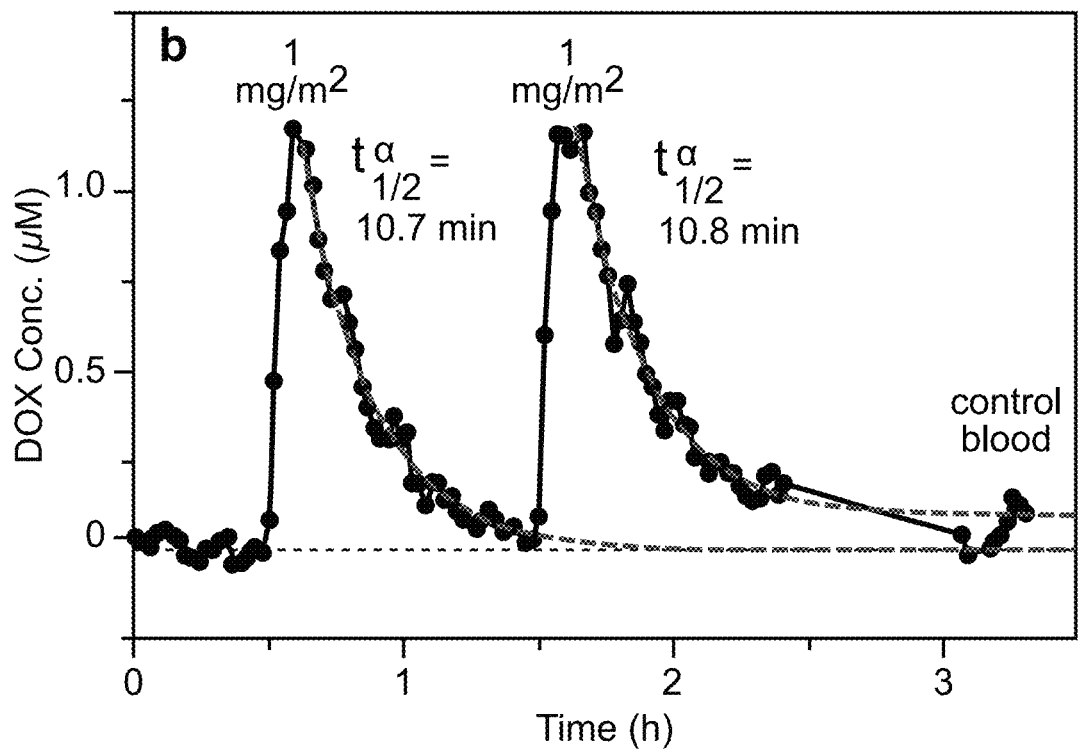
Figure 12:
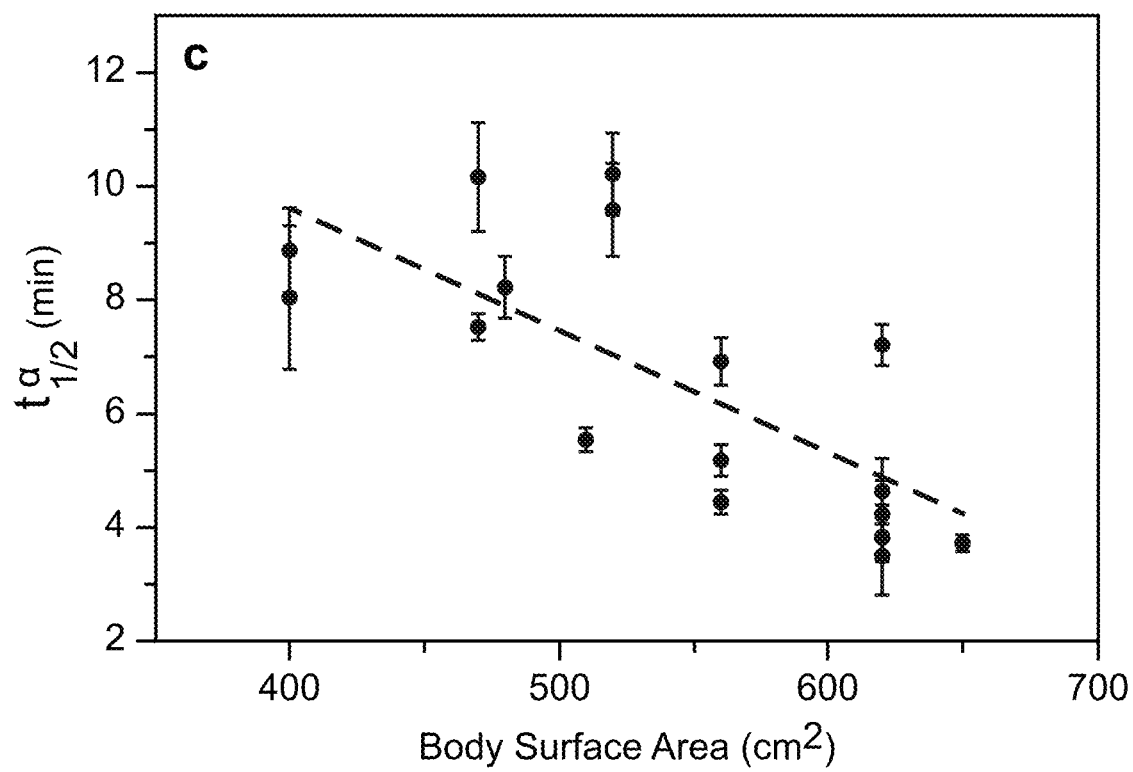
Figure 12:
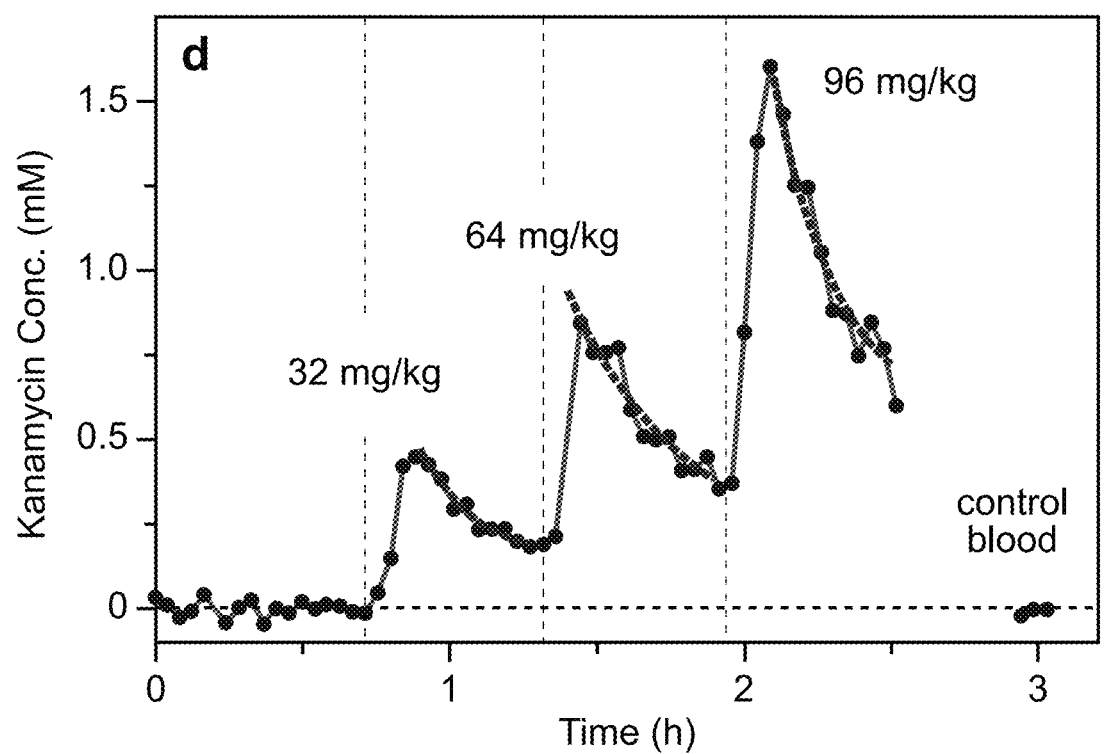
Figure 13:
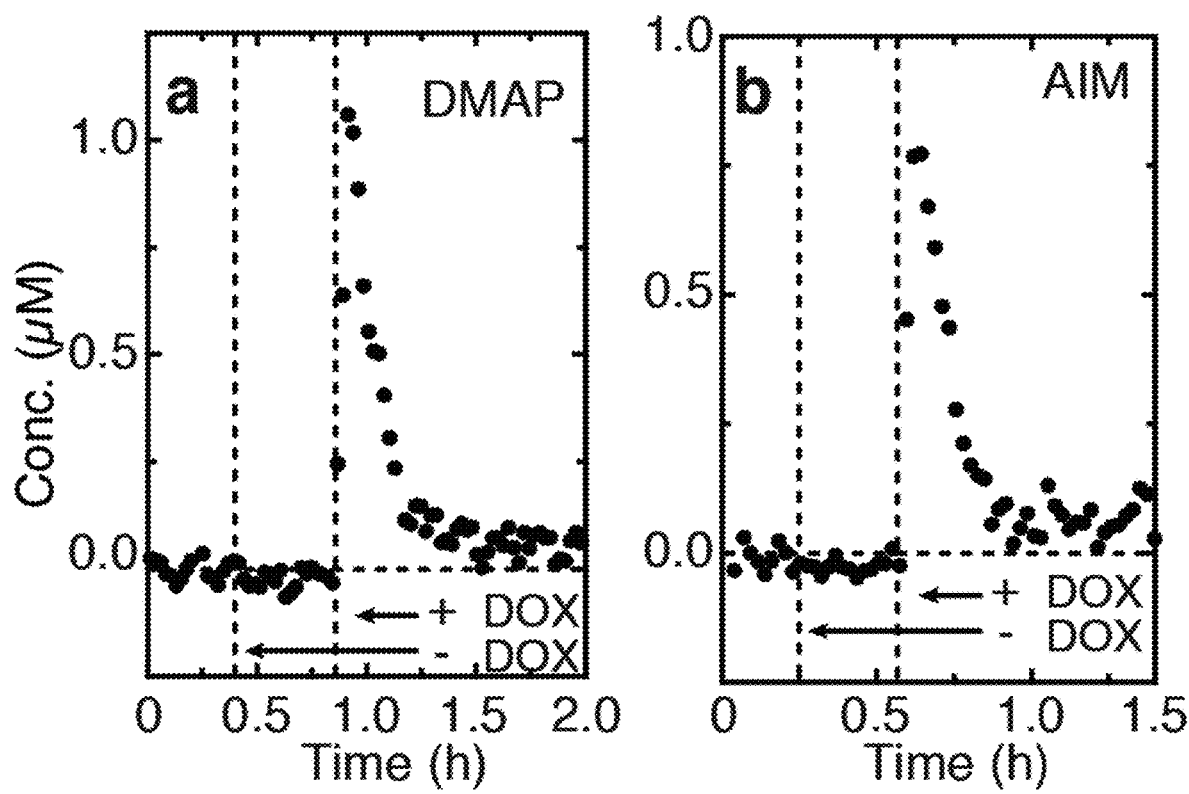
FIG. 13 provides graphs demonstrating sensor specificity in vivo for an embodiment of a MEDIC system according to the present disclosure. Rats were subjected to chemotherapy cocktails (a) DMAP (MTC, DTIC, and CDDP) and (b) AIM (Ifex and Mesna) in the absence or presence of DOX. No observable response was detected to either cocktail in the absence of DOX but a significant response was observed in its presence, confirming MEDIC specificity in vivo.

To demonstrate continuous real-time measurement of analyte concentrations in a living animal, DOX was injected intravenously into anesthetized Sprague-Dawley rats while blood was continuously drawn into the chip using an indwelling catheter. This ensures full systemic circulation prior to measurement, and owing to the low flow rate (750 µL·h$^{-1}$), recirculation of blood back into the rat is not necessary. A rat with a body surface area of 620 cm$^2$ was dosed with increasing DOX concentrations (0-2 mg·m$^{-2}$) over 4.5 hours (FIG. 12, Panel A). Vehicle-only injection (negative control) yielded no observable signal change. The lowest DOX dose (0.1 mg·m$^{-2}$), in contrast, resulted in a peak in vivo concentration of 0.13 µM, while doses of 0.2, 0.6 and 2 mg·m$^{-2}$ resulted in peak concentrations of 0.3, 1.0 and 2.5 µM, respectively—a therapeutically-relevant range for human dosing. A final measurement made on blood collected prior to the first dosing confirmed minimal drift (0.1 µM) during the experiment (FIG. 12, Panel A). Importantly, MEDIC exhibited remarkable specificity; no signal was observed from rats injected with AIM (Ifex and Mesna) and DMAP (DTIC, MTC and CDDP) drug cocktails unless DOX was added to the mixture. (FIG. 13).

The disclosed MEDIC system allows for real-time measurement of key pharmacokinetic parameters. To demonstrate this, a rat was dosed with two DOX injections (1 mg·m$^{-2}$) an hour apart and the in vivo concentration profiles were measured (FIG. 12, Panel B). MEDIC detected equivalent peak concentrations (1.17 and 1.16 µM) and alpha-phase half-life values ($t_{1/2}^{\alpha}$=10.7±0.5 and 10.8±1 min) after each injection, consistent with previously published values. As an illustration of the potential impact of this technology, significant pharmacokinetic variability (Pearson correlation coefficient=−0.73) was observed when measuring $t_{1/2}^{\alpha}$ as a function of body surface area across nine rats (FIG. 12, Panel C). Similar variability has been reported in human patients, and can result in dramatically different patient outcomes. By enabling direct measurement of these key pharmacokinetic parameters, MEDIC provides a potentially powerful means of eliminating such variability.

Example 5

Adaptation to Other Targets

MEDIC can be adapted to detect a variety of targets. To demonstrate this, the aptamer probe was exchanged to perform continuous detection of the antibiotic kanamycin. A calibration curve was obtained (FIG. 5), then doses of 32, 64 and 96 mg·kg$^{-1}$ were serially injected, followed by a baseline control. Peak concentrations of 0.45, 0.85 and 1.6 mM, respectively, were observed (FIG. 12, Panel D), and $t_{1/2}^{\alpha}$ of 7.2, 10 and 9 minutes were measured, similar to previously-reported values for this drug. The baseline control sample revealed minimal drift throughout the experiment (<0.01 mM). Unlike DOX, kanamycin concentrations do not return to baseline, because much of the clearance of this drug occurs in the beta phase ($t_{1/2}^{\beta}$≈2-3 h), which is considerably longer than the dosing interval (40 min) utilized in these examples.

Example 6

Figure 14:
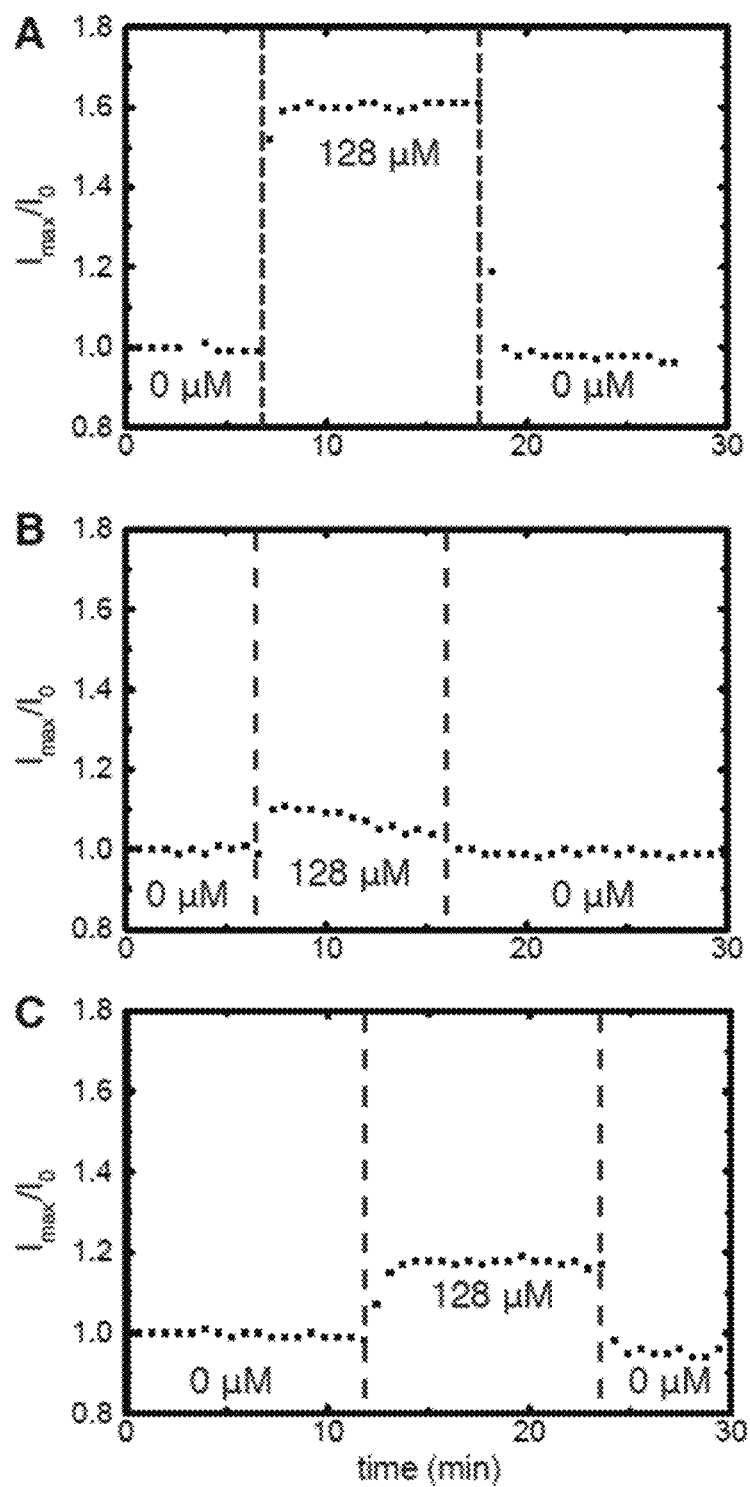
FIG. 14 provides graphs showing desensitization of a conformation switching aptamer probe upon whole blood exposure as measured by peak current gain step responses for target-doped samples. (Panel A) The sensor quickly equilibrates in response to 128 µM procaine in SSC buffer with 60% signal gain and returns to baseline rapidly. (Panel B) The same concentration in whole blood results in significantly less gain at ~10% for the same device. The signal also begins to recede before the input is switched to procaine-free whole blood. (Panel C) The sensor is challenged with a 128 µM procaine step in buffer after whole blood exposure. Although the gain has doubled to ~20%, it remains significantly less than preexposure level, indicating biofouling of the sensor surface.

Desensitzation and Signal Degradation Due to Whole Blood Exposure of Cocaine/Procaine Binding Aptamer The cocaine/procaine binding aptamer described above was initially challenged with 128 µM target doped in pure 1×SSC buffer to represent ideal sensing conditions. First, 1×SSC buffer is injected into the device through at 6 mL·h$^{-1}$. Square-wave voltammograms (SWV) were acquired every thirty seconds with the peak faradic current recorded as a function of time. After seven minutes of collecting baseline signals, the input is switched to target-doped buffer. After ten minutes, the input is reverted to pure buffer. The initial gain of 60% is observed and rapid equilibration is achieved in association and disassociation with a $k_{on}$~1.6×10$^2$ s$^{-1}$·M$^{-1}$ and $k_{off}$~3.1×10$^{-2}$ s$^{-1}$, yielding a $k_D$~190 µM which is consistent with reported values. However, after exposing the sensor to whole blood at room temperature for ~1 h, and then challenging with 128 μM target-doped blood, the gain was significantly lower at ~10% and declining (FIG. 14, Panel B). This is an effect seen to varying degrees in prior work in serum and whole blood. Returning the sensor directly to buffer, the baseline is reinitialized and the sensor is again challenged with 128 μM target-doped buffer (FIG. 14, Panel C). This time, the sensor yielded ~20% gain, though higher than in whole blood, significantly less than the initial response. This result suggests that whole blood exposure, in addition to reducing the gain in situ, also fouls the surface in a manner that is not recoverable by simple re-immersion into buffer, substantiating the need to prevent surface fouling.

Example 7

Simulation of Target and Interferent Transport

In the device channel, the Reynolds number was calculated to be ~0.1, assuming a viscosity of 4 mPa·s and density of 1060 kg·m$^{-3}$ at a flow speed of 1 mm·s$^{-1}$, indicating laminar flow under normal conditions. It was thus expected that vertical stacking of sample and buffer flow streams may be achieved without mixing, permitting a controlled analyte diffusion layer.

To obtain an estimate of the relative transport of target analyte and non-target interferents, a constant planar-source diffusion model is assumed, wherein the concentration C, at a distance y from the source is given by, $$\frac{C(y, t > 0)}{C_0} = \text{erfc}\left(\frac{x}{\sqrt{4Dt}}\right).$$

Figure 15:
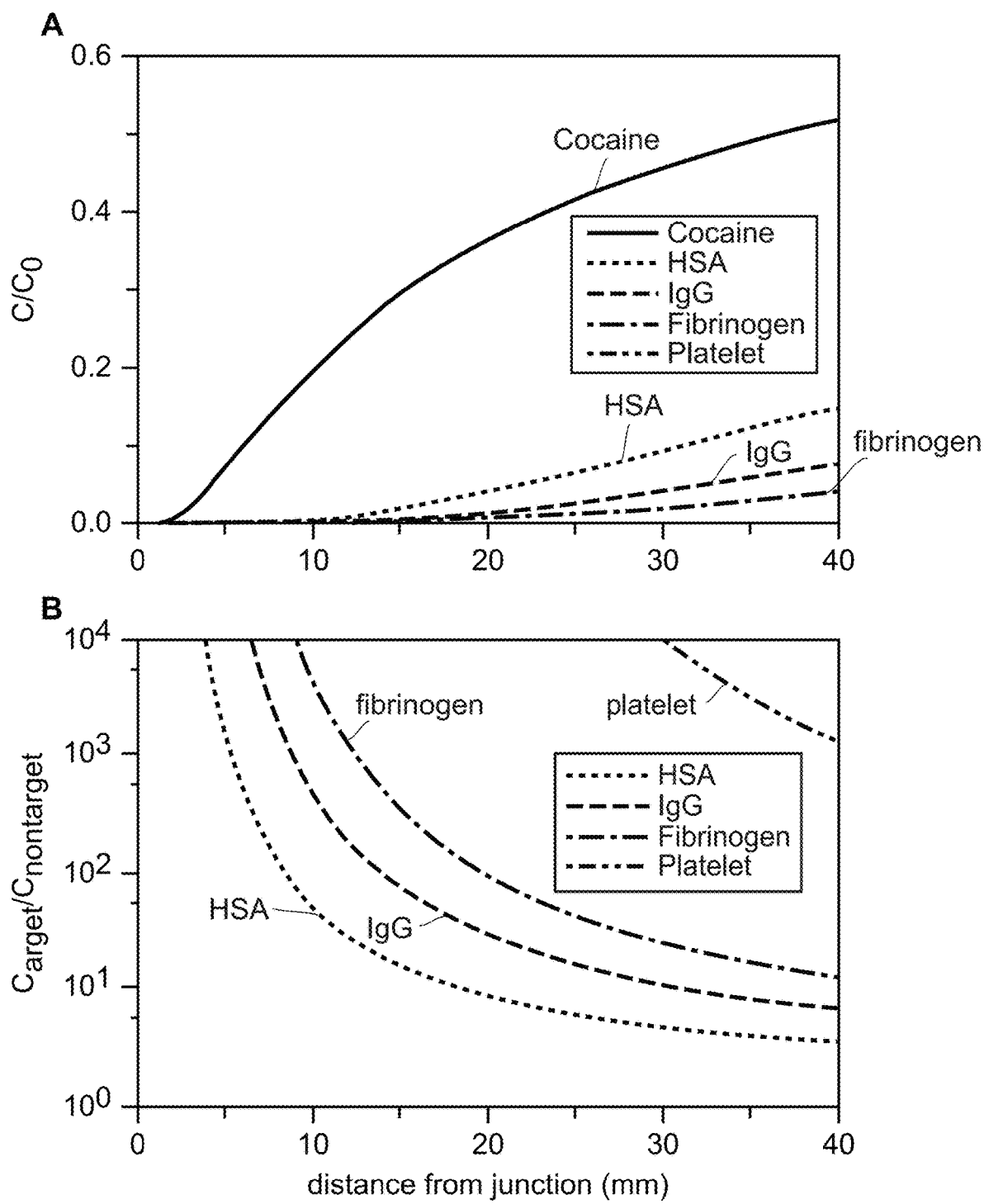
FIG. 15 provides graphs showing Target and interferant diffusion and enrichment. (Panel A) Constant planar-source estimate for diffusion of target and interferants across 100 µm diffusion barrier along microchannel as a fraction of respective source concentrations. (Panel B) Enrichment factor of procaine target against interferants through 100 µm diffusion barrier.

D is the diffusion constant of the given target or interferent, and $C_0$ is its initial concentration. The diffusion constant of the target cocaine was taken as $3\times10^{-10}$ m$^2$·s$^{-1}$. A sample of blood interferents reported to be active in biofouling include human serum albumin (HSA), Immunoglobulin G (IgG), fibrinogen, and platelets, with respective diffusivities of 6, 4, 3 and $1\times10^{-10}$ m$^2$·s$^{-1}$. To project this estimate along the flow channel, the concentration as a function of position may be approximated by multiplying the time and the average flow velocity in the channel. Doing so for the above species across a 100 μm diffusion barrier at 1 mm·s$^{-1}$ demonstrates the selective passage of smaller, higher diffusivity species (FIG. 15, Panel A). A trade-off between non-target suppression and target retention is evident. Nevertheless, since the diffusivities of the target and smaller interferents differ by nearly an order of magnitude, significant suppression of interferents is possible with a modest expense in target concentration. For example, at region where >99% of HSA is rejected >20% of the target is retained. Platelets, differing in diffusivity by more than two orders, are essentially untransmitted across this length scale. By taking the ratio of the target and non-target concentration fractions along the channel, the enrichment is obtained (FIG. 15, Panel B), demonstrating a usable range across a reasonable channel length with ten-fold enrichment over HSA, hundred-fold enrichment over fibrinogen, and greater than 10,000-fold enrichment over platelets approximately 2 cm from the junction.

Figure 16:
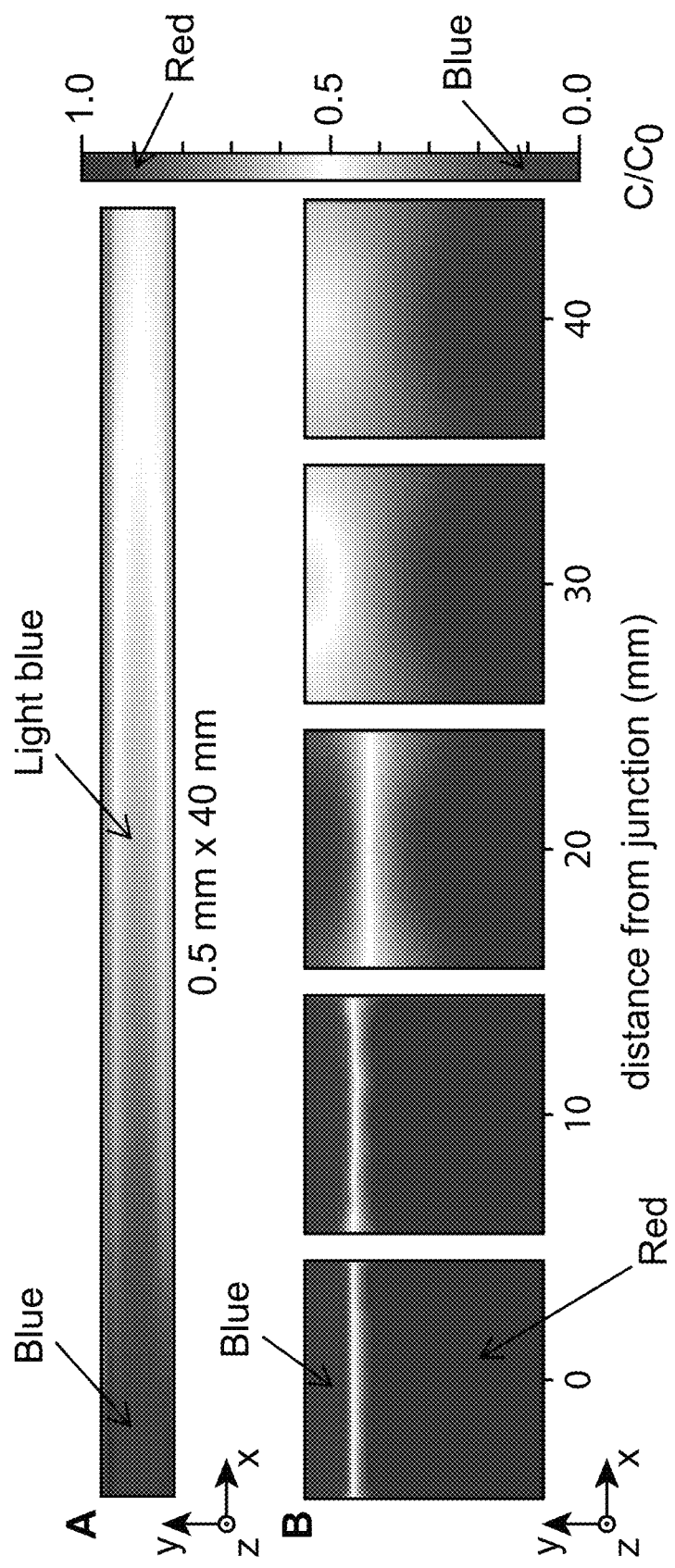
FIG. 16 provides a 3D simulation of target transport. Steady Poiseuille flow and convection diffusion equations are solved for the 3D microchannel from the flow-stream junction to the outlet. (Panel A) xy cross-section at the electrode plane (ceiling) of the device indicating the fraction of procaine transferred from source stream. (Panel B) yz cross-sections at 10 mm intervals along the channel from the junction, demonstrating the migration of target from source stream to buffer stream.

An improved estimate of the transport of cocaine is obtained for steady Poiseuille flow in the square microchannel channel using COMSOL Multiphysics. First solving for the velocity field and then the convection diffusion equation yields the concentration field throughout the channel (FIG. 16). An xy cross section is taken at the top the channel in the plane of the electrodes (FIG. 16, Panel A, scaled at 20% in x with respect to y). The cross-section confirms the expected transport fraction to range up to ~50% by 4 cm with parabolic isolines. Examining yz sections along the channel (FIG. 16, Panel B) demonstrates the diffusion of cocaine from the cocaine-rich flow stream to the initially pure buffer stream.

Example 8

Sensor Performance Enhancement Via Diffusion Filter

Long term sensor performance may be important for applications in continuous monitoring. By rejecting the transport of a significant fraction of blood proteins active in surface biofouling, and eliminating the physical occlusion of the sensor by the tremendous background of platelets and erythrocytes, while still permitting the passage of small-molecule targets, the continuous diffusion filter (CDF) may improve performance and greatly extend sensor lifetime.

Figure 17:
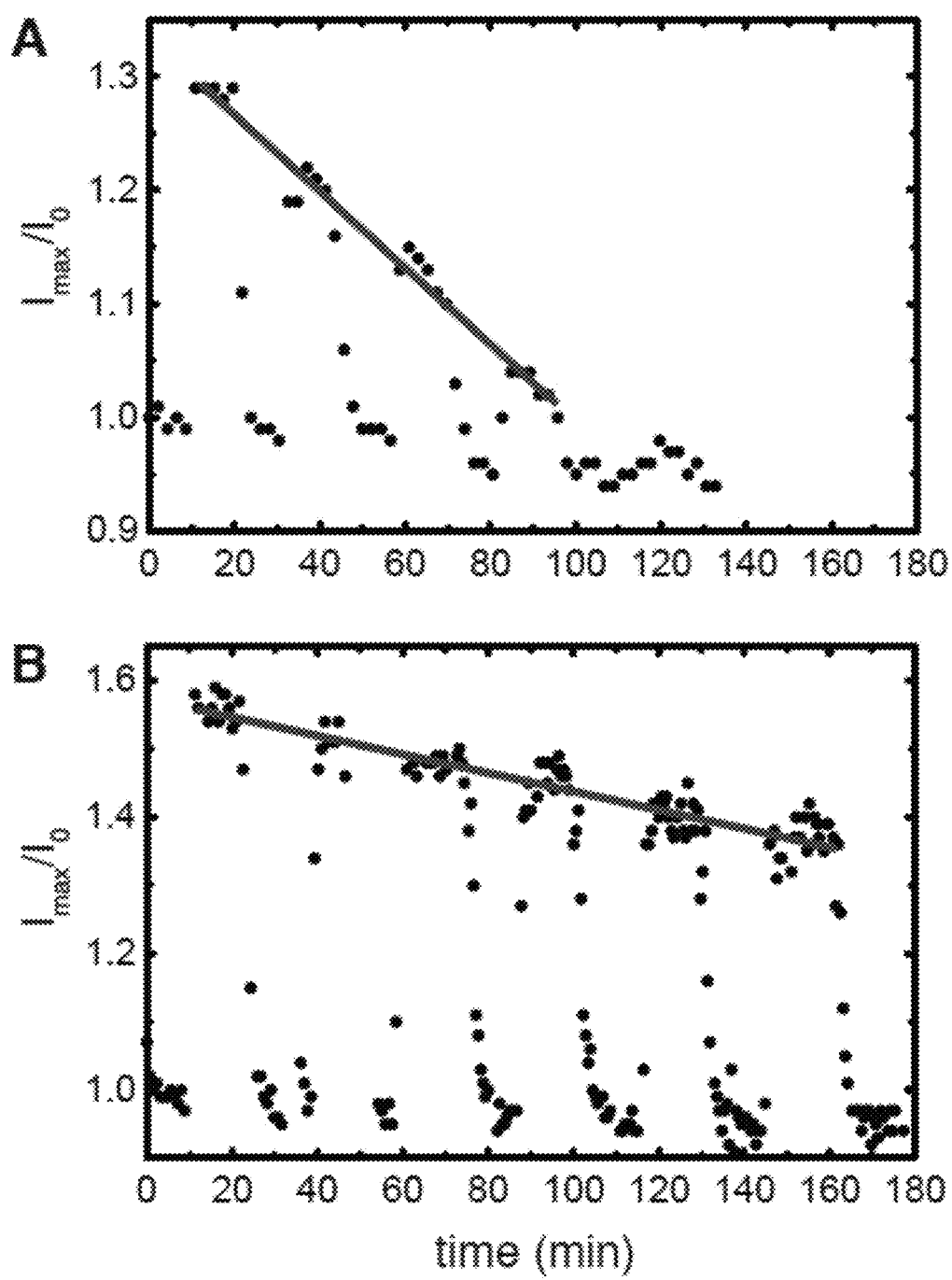
FIG. 17 provides graphs showing signaling degradation and preservation during continuous monitoring in whole blood. Continuous monitoring step responses to target in whole blood. (Panel A) Response to 512 µM steps without CDF. Note that the signal gain degrades at ~0.34% min$^{-1}$, resulting in loss of response in less than two hours. (Panel B) Response to 2 mM steps with CDF. The rate of signal loss is decreased to ~0.14% min$^{-1}$, extending the sensor lifetime to 240% of its potential in the absence of the CDF.

To demonstrate this capability, the performance of the MEDIC device with and without the continuous diffusion filter (CDF) was compared (FIG. 17). Whole blood is continuously injected into the devices, switching periodically between target-free and target-doped samples to elicit step responses. For the control without the diffusion barrier (FIG. 17, Panel A), 0.5 mM target is cycled, giving rise to an initial gain of ~30% and falling to background levels by 2 hours. Applying the CDF (FIG. 17, Panel B) and 2 mM target cycles, the gain at ~60%, begins to decrease, at a lower rate. To approximate the rate of signal loss a least-squares linear fit is applied to the data collected in the presence of target-doped solution. In the control, signal is degraded at a rate of 0.34% min$^{-1}$, while in the CDF, this rate is 0.14% min$^{-1}$. The implication of this is that a sensor yielding an initial gain of 20% is expected to last less than 1 hour before the signal is indistinguishable from the background. However, the same sensor initially responding with signal gain of 20%, could sustain approximately 2.4 hours in the CDF. This improvement factor may be further improved by optimization of flow parameters and native electrode stability.

Sensor lifetime could be extended though systematic optimization of the flow parameters and by improving the inherent stability of the immobilized probe and passivated layer through use of multi-thiol-linked termini.

The CDF confers additional capability to small molecule sensing. For example, multiple targets could be immobilized on the existing or expanded electrode array, allowing for multiplexed real time sensing for a number of existing aptamer-target pairs. Further, aptamers of optimal performance at non-physiological pH or temperatures could be implemented on the device by controlling buffer conditions and applying a temperature controlled surface-indeed the cocaine/procaine aptamer employed in this work loses affinity for its target at 37° C. but performs well at room temperature. The CDF can also serve as a tool to expand the dynamic range of the sensor by controlling the diffusion layer thickness or sensing at different positions along the gradient. This effect could also be achieved by engineering the stability of the binding or non-binding states of the aptamer switch.

What is claimed is:

1. A method of determining an in vivo concentration of an analyte in a biological fluid, the method comprising:
flowing the biological fluid from a living subject;
contacting the biological fluid or a component thereof with a signaling probe comprising a conformation switching aptamer and a detectable label, wherein the signaling probe is immobilized on a working electrode of an electrochemical sensor, wherein the working electrode generates a detectable signal based on a property of the detectable label, wherein specific binding of the analyte to the conformation switching aptamer causes a change in the detectable signal generated by the working electrode, wherein the detectable label is a redox reporter and the property is a change in the rate of charge transfer or impedance at the working electrode;
detecting detectable signals during a first period of time in response to a binding event between the analyte, when present in the biological fluid, and the signaling probe, wherein the detecting comprises:
voltammetrically interrogating the working electrode during the first period of time with a first waveform to obtain a first signal;
voltammetrically interrogating the working electrode during the first period of time with a second waveform to obtain a second signal;
combining the first signal and the second signal to obtain an adjusted signal for the first period of time, wherein the adjusted signal for the first period of time has a greater magnitude than the first signal and the second signal; and
determining the in vivo concentration of the analyte during the first period of time based on the adjusted signal for the first period of time.

2. The method of claim 1, wherein the signaling probe is immobilized in a channel of a microfluidic device.

3. The method of claim 2, wherein the channel is configured to receive a sample stream comprising the biological fluid and a buffer stream, and wherein the microfluidic device is further configured to provide a stacked laminar flow of the sample stream and buffer stream in the channel, when present in the microfluidic device, such that the sample stream is positioned adjacent to, and in contact with, the buffer stream.

4. The method of claim 3, wherein the stacked laminar flow is a vertically stacked laminar flow.

5. The method of claim 3, wherein the stacked laminar flow is a horizontally stacked laminar flow.

6. The method of claim 3, wherein the height of the channel is from about 1 μm to about 1000 μm.

7. The method of claim 3, wherein the sample stream has a first flow rate, the buffer stream has a second flow rate, and the ratio of the second flow rate to the sum of the first and second flow rates is from about 0.1:1 to about 1:1.

8. The method of claim 1, comprising administering a pharmacologically active agent based on the determined in vivo concentration of the analyte.

9. The method of claim 8, wherein the administering is automatic.

10. The method of claim 1, wherein the analyte is a small molecule drug or a metabolite thereof, and the method further comprises:
administering a small molecule drug to the subject; and following said determining, administering an adjusted dose of the small molecule drug to the subject based on the determined in vivo concentration of the analyte.

11. A method of determining a concentration of an analyte in a sample fluid, the method comprising:
flowing the sample fluid;
contacting the sample fluid or a component thereof with a signaling probe comprising a redox reporter, wherein the signaling probe produces a detectable signal based on specific binding of the signaling probe to the analyte when present in the sample fluid and change in the rate of charge transfer or impedance at a working electrode of an electrochemical sensor that the signaling probe is immobilized on, and wherein the signaling probe further comprises a conformation switching aptamer;
detecting detectable signals during a first period of time in response to a binding event between the analyte, when present in the sample fluid, and the signaling probe, wherein the detecting comprises:
voltammetrically interrogating the working electrode during the first period of time with a first waveform to obtain a first signal;
voltammetrically interrogating the working electrode during the first period of time with a second waveform to obtain a second signal;
combining the first signal and the second signal to obtain an adjusted signal for the first period of time, wherein the adjusted signal for the first period of time has a greater magnitude than the first signal and the second signal; and
determining the concentration of the analyte during the first period of time based on the adjusted signal for the first period of time.

12. The method of claim 1, wherein voltammetrically interrogating the working electrode comprises square-wave voltammetry (SWV).

13. The method of claim 1, wherein voltammetrically interrogating utilizes alternating current voltammetry, linear sweep voltammetry, or differential pulse voltammetry.

14. The method of claim 11, wherein voltammetrically interrogating the working electrode comprises square-wave voltammetry (SWV).

15. The method of claim 11, wherein voltammetrically interrogating utilizes alternating current voltammetry, linear sweep voltammetry, or differential pulse voltammetry.

16. The method of claim 1, wherein the redox reporter comprises a redox-active metal center.

17. The method of claim 16, wherein the redox reporter is a redox-active organic molecule.

18. The method of claim 1, wherein the detectable label is covalently linked to the conformation switching aptamer.

19. The method of claim 1, wherein the adjusted signal for the first period of time is the difference of the first signal and the second signal divided by the average of the first signal and the second signal.

20. The method of claim 1, wherein the method further comprises:
continuing to flow the biological fluid from the living subject;
continuing to contact the biological fluid or a component thereof with the signaling probe;
detecting detectable signals during a second period of time in response to a binding event between the analyte, when present in the biological fluid, and the signaling probe, wherein the detecting comprises:
voltammetrically interrogating the working electrode during the second period of time with the first waveform to obtain a third signal;
voltammetrically interrogating the working electrode during the second period of time with the second waveform to obtain a fourth signal;
combining the third signal and the fourth signal to obtain an adjusted signal for the second period of time;
determining the in vivo concentration of the analyte during the second period of time based on the adjusted signal for the second period of time.

21. The method of claim 20, wherein the second period of time begins at least 5 minutes after the first period of time ends.

22. The method of claim 21, wherein the second period of time begins at least 1 hour after the first period of time ends.

* * * * *

UNITED STATES PATENT AND TRADEMARK OFFICE
CERTIFICATE OF CORRECTION

| | | |
|---|---|---|
| PATENT NO. | : 12,016,682 B2 | |
| APPLICATION NO. | : 14/768134 | |
| DATED | : June 25, 2024 | |
| INVENTOR(S) | : Brian Scott Ferguson et al. | |

It is certified that error appears in the above-identified patent and that said Letters Patent is hereby corrected as shown below:

In the Drawings

On Sheet 16 of 18, in figure 15-Panel B, Line 1 (Y-axis), delete "$C_{areget}$" and insert -- $C_{target}$ --.

In the Specification

In Column 11, Line 1, delete "measureable" and insert -- measurable --.

In Column 14, Line 54, delete "strepavidin" and insert -- streptavidin --.

In Column 15, Line 2, delete "principal," and insert -- principle, --.

In Column 19, Line 55, delete "e.g," and insert -- e.g., --.

In Column 21, Lines 18-19, delete "voltametrically" and insert -- voltammetrically --.

In Column 26, Line 65, delete "plasma." and insert -- plasma; and --.

In Column 27, Line 40, delete "addition" and insert -- additional --.

In Column 28, Line 10, delete "defined" and insert -- define --.

In Column 36, Lines 25-27, delete

"$$I = -F\frac{d[MB]}{dt} = F(k_1[MB] - k_{-1}[-leucoMB]),$$"

and insert

-- $$I = -F\frac{d[MB]}{dt} = F(k_1[MB] - k_{-1}[leucoMB]),$$ --.

Signed and Sealed this
Twenty-second Day of October, 2024

*Katherine Kelly Vidal*
Katherine Kelly Vidal
*Director of the United States Patent and Trademark Office*

CERTIFICATE OF CORRECTION (continued)
U.S. Pat. No. 12,016,682 B2

In Column 39, Lines 35-36, delete "flourescent" and insert -- fluorescent --.

In Column 42, Line 9, delete "mixture. (FIG. 13)." and insert -- mixture (FIG. 13). --.

In Column 42, Line 50, delete "Desensitzation" and insert -- Desensitization --.

SEQUENCE LISTING

<160> NUMBER OF SEQ ID NOS: 3

<210> SEQ ID NO 1
<211> LENGTH: 28
<212> TYPE: DNA
<213> ORGANISM: Artificial Sequence
<220> FEATURE:
<223> OTHER INFORMATION: synthetic aptamer sequence

<400> SEQUENCE: 1
accatctgtg taaggggtaa ggggtggt                                    28

<210> SEQ ID NO 2
<211> LENGTH: 26
<212> TYPE: DNA
<213> ORGANISM: Artificial Sequence
<220> FEATURE:
<223> OTHER INFORMATION: synthetic aptamer sequence

<400> SEQUENCE: 2
gggacttggt ttaggtaatg agtccc                                      26

<210> SEQ ID NO 3
<211> LENGTH: 32
<212> TYPE: DNA
<213> ORGANISM: Artificial Sequence
<220> FEATURE:
<223> OTHER INFORMATION: synthetic aptamer sequence

<400> SEQUENCE: 3
agacaaggaa aatccttcaa tgaagtgggt cg                               32